(12) United States Patent
Sloan

(10) Patent No.: US 11,766,380 B2
(45) Date of Patent: *Sep. 26, 2023

(54) AUTOMATED GENERATION OF CONTROL SIGNALS FOR SEXUAL STIMULATION DEVICES

(71) Applicant: Brian Sloan, Mercer Island, WA (US)

(72) Inventor: Brian Sloan, Mercer Island, WA (US)

(73) Assignee: BOON INTELLECTUAL PROPERTY LAW, PLLC

( * ) Notice: Subject to any disclaimer, the term of this patent is extended or adjusted under 35 U.S.C. 154(b) by 0 days.

This patent is subject to a terminal disclaimer.

(21) Appl. No.: 18/183,948

(22) Filed: Mar. 14, 2023

(65) Prior Publication Data

US 2023/0210715 A1 Jul. 6, 2023

Related U.S. Application Data

(63) Continuation of application No. 17/737,974, filed on May 5, 2022, now Pat. No. 11,607,366, which is a continuation-in-part of application No. 17/534,155, filed on Nov. 23, 2021, now Pat. No. 11,478,398, which is a continuation of application No. 16/861,014, filed on Apr. 28, 2020, now Pat. No. 11,185,465, which is a continuation-in-part of application No. 16/214,030, filed on Dec. 7, 2018, now Pat. No. 10,638,174, which is a continuation-in-part of application No. 16/139,550, filed on Sep. 24, 2018, now Pat. No. 10,576,013.

(51) Int. Cl.
*A61H 19/00* (2006.01)
*G06F 16/783* (2019.01)

(52) U.S. Cl.
CPC ............. *A61H 19/00* (2013.01); *A61H 19/32* (2013.01); *G06F 16/783* (2019.01); *A61H 2201/501* (2013.01); *A61H 2201/5058* (2013.01); *A61H 2230/825* (2013.01)

(58) Field of Classification Search
CPC .. A61H 19/00; A61H 19/32; A61H 2201/501; A61H 2201/5058; A61H 2201/5097; A61H 2230/825
See application file for complete search history.

(56) References Cited

U.S. PATENT DOCUMENTS

| | | | |
|---|---|---|---|
| 8,308,631 B2 | 11/2012 | Kobashikawa et al. | |
| 10,143,618 B2 | 12/2018 | Cambridge | |
| 11,607,366 B2 * | 3/2023 | Sloan | ............... H04N 21/23418 |
| 2015/0305971 A1 | 10/2015 | Davis et al. | |

* cited by examiner

*Primary Examiner* — Christine H Matthews
(74) *Attorney, Agent, or Firm* — BOON INTELLECTUAL PROPERTY LAW, PLLC; Brian S. Boon

(57) ABSTRACT

A system and method for automated generation of control signals for sexual stimulation devices from usage history and other data. The system and method involve analyzing historical usage and other data for a user for a device or devices, processing the data through machine learning algorithms, and generating new or recombined patterns of stimulation based on the outputs from the machine learning algorithms. The resulting automated control signals represent partially or fully customized stimulation for a given user which evolve over time as the user continues to use the device or devices.

15 Claims, 25 Drawing Sheets

AUTOMATED GENERATION OF CONTROL SIGNALS FOR SEXUAL STIMULATION DEVICES

CROSS-REFERENCE TO RELATED APPLICATIONS

Priority is claimed in the application data sheet to the following patents or patent applications, each of which is expressly incorporated herein by reference in its entirety:
Ser. No. 17/737,974
Ser. No. 17/534,155
Ser. No. 16/861,014
Ser. No. 16/214,030
Ser. No. 16/139,550

BACKGROUND OF THE INVENTION

Field of the Art

The present invention is in the field of computer control systems, and more specifically the field of control systems for sexual stimulation devices.

Discussion of the State of the Art

In the field of sexual stimulation devices, control systems are rudimentary, and primarily limited to pre-programmed, selectable stimulation routines. Where customization is possible, it is available only through manual programming of the device.

What is needed is a system and method for automated generation of control signals for sexual stimulation devices from usage history and other data.

SUMMARY OF THE INVENTION

Accordingly, the inventor has conceived, and reduced to practice, a system and method for automated generation of control signals for sexual stimulation devices from usage history and other data. The system and method involve analyzing historical usage and other data for a user of a device, processing the data through a trained machine learning algorithm or statistical analyzer, and generating new or recombined patterns of stimulation based on the outputs from the machine learning algorithm or statistical analysis. The resulting automated control signals represent partially or fully customized stimulation for a given user which evolve over time as the user continues to use the device. In some embodiments, the machine learning algorithm will be trained on usage data from a large number of users of the same device or similar devices or the statistical analysis will be performed on such usage data.

According to a preferred embodiment, a system for automated generation of control signals for sexual stimulation devices from usage data is disclosed, comprising: a computing device comprising a memory, a processor, a non-volatile data storage device, and a wireless networking device; a user profile database on the non-volatile data storage device, the usage profile database comprising a plurality of user profiles, each profile comprising a plurality of user characteristics and feedback for a plurality of stimulation aspects for a given type of stimulation device; a machine learning algorithm operating on the computing device trained to identify patterns among the user profiles and configured to output stimulation profiles based an input of a user profile; and an auto-pilot application comprising a first plurality of programming instructions stored in the memory which, when operating on the processor, causes the computer system to: receive a user profile for a user of a stimulation device of the same type as the given type of stimulation device; process the user profile through the machine learning algorithm to obtain a stimulation profile for the user associated with the user profile; generate control signals for the stimulation device based on the stimulation profile; connect to a device controller for the stimulation device using the wireless networking device and output the control signals to the device controller using the wireless networking device; receive feedback associated with the stimulation profile; update the user profile with the feedback; and repeat the above-listed processes of the auto-pilot application for the updated user profile.

According to another preferred embodiment, a system for automated generation of control signals for sexual stimulation devices from usage data is disclosed, comprising: a distributed computing network comprising a plurality of networked computers, each computer comprising a memory, a processor, a non-volatile data storage device, and a wireless networking device; a user profile database on a non-volatile data storage device of one of the plurality of networked computers, the usage profile database comprising a plurality of user profiles, each profile comprising a plurality of user characteristics and feedback for a plurality of stimulation aspects for a given type of stimulation device; a machine learning algorithm operating on one of the plurality of networked computers trained to identify patterns among the user profiles and configured to output stimulation profiles based an input of a user profile; and an auto-pilot application operating on one of the plurality of networked computers, the auto-pilot application comprising a first plurality of programming instructions stored in the memory of the same networked computer which, when operating on the processor of the same networked computer, causes that same computer to: receive a user profile for a user of a stimulation device of the same type as the given type of stimulation device; process the user profile through the machine learning algorithm to obtain a stimulation profile for the user associated with the user profile; generate control signals for the stimulation device based on the stimulation profile; connect to a device controller for the stimulation device using the wireless networking device and output the control signals to the device controller using the wireless networking device; receive feedback associated with the stimulation profile; update the user profile with the feedback; and repeat the above-listed processes of the auto-pilot application for the updated user profile.

According to another preferred embodiment, a method for automated generation of control signals for sexual stimulation devices from usage data, comprising: storing a user profile database on a non-volatile data storage device of a computer, the usage profile database comprising a plurality of user profiles, each profile comprising a plurality of user characteristics and feedback for a plurality of stimulation aspects for a given type of stimulation device; training a machine learning algorithm operating on a computer to identify patterns among the user profiles and configuring the machine learning algorithm to output stimulation profiles based an input of a user profile; using an auto-pilot application operating on a computer to: receive a user profile for a user of a stimulation device of the same type as the given type of stimulation device; process the user profile through the machine learning algorithm to obtain a stimulation profile for the user associated with the user profile; generate control signals for the stimulation device based on the stimulation profile; connect to a device controller for the stimulation device using the wireless networking device and output the control signals to the device controller using the wireless networking device; receive feedback associated with the stimulation profile; update the user profile with the feedback; and repeat the above-listed processes of the auto-pilot application for the updated user profile.

According to an aspect of an embodiment, the feedback comprises sensor data from a sensor on the stimulation device received from the controller via the wireless networking device.

According to an aspect of an embodiment, the auto-pilot application is configured to connect via the wireless networking device to an external device other than the stimulation device, and the feedback comprises data from a sensor on that external device.

According to an aspect of an embodiment, a user interface comprising operational controls for the stimulation device or rating controls for the stimulation profile is used to provide the feedback, which is received from the user via the user interface.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

DETAILED DESCRIPTION OF THE DRAWING FIGURES

Figure 1:
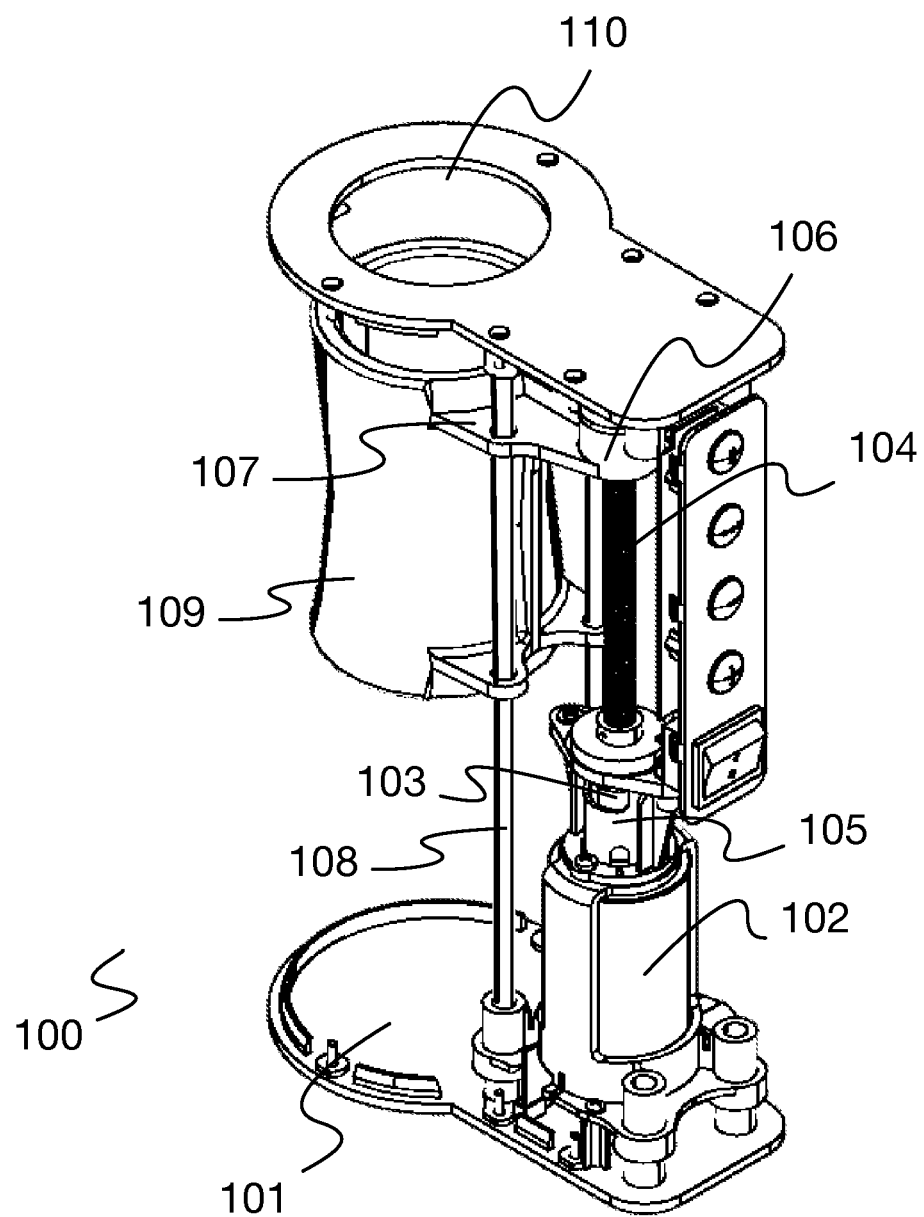
FIG. 1 shows the internal workings of an exemplary sexual stimulation device.

The inventor has conceived, and reduced to practice, a system and method for automated generation of control signals for sexual stimulation devices from usage history and other data. The system and method involve analyzing historical usage and other data for a user for a device or devices, processing the data through machine learning algorithms, and generating new or recombined patterns of stimulation based on the outputs from the machine learning algorithms. The resulting automated control signals represent partially or fully customized stimulation for a given user which evolve over time as the user continues to use the device or devices. In some embodiments, the machine learning algorithm will be trained on usage data from a large number of users of the same device or similar devices or the statistical analysis will be performed on such usage data.

This automated generation of control signals from historical usage and other data, and evolution of the control signals over time, acts as a sort of "autopilot" for sexual stimulation devices such that a priori programming or manual programming of the devices either not required at all or is minimal in nature. The device can simply be turned on and stimulation will be automatically customized to the user's preferences with little or no input on the user's part.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself.

Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

Conceptual Architecture

Figure 7:
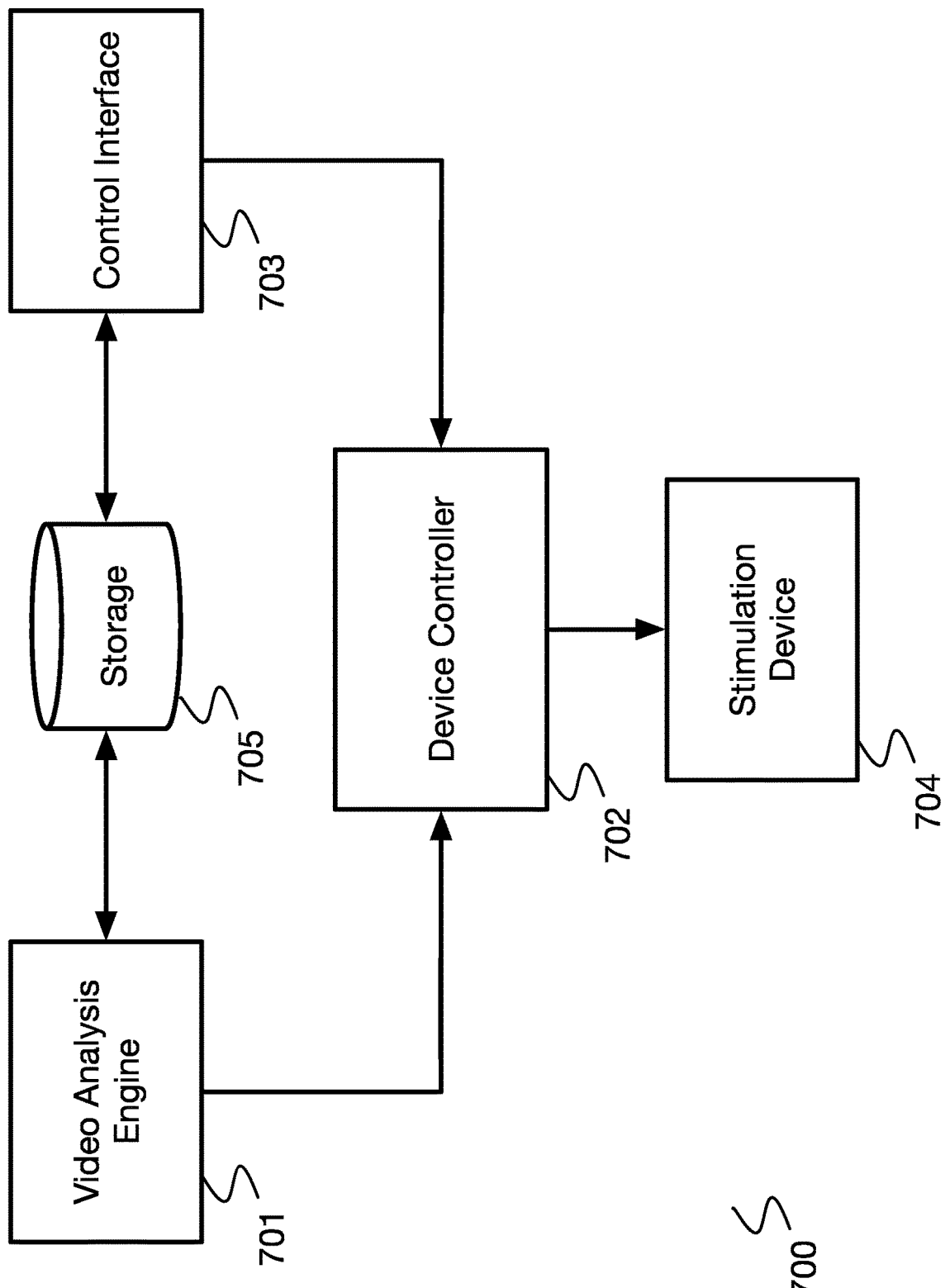
FIG. 7 is a block diagram of an exemplary synchronized video control system for sexual stimulation devices.

FIG. 7 is a block diagram of an exemplary synchronized video control system for sexual stimulation devices 700. In a preferred embodiment, a video analysis engine 701 inputs a video of sexual activity, parses the video into at least the components of movement corresponding to the sexual activity shown in the video, and outputs signals containing the parsed video information to a device controller 702. A control interface 703 allows the user to enter a profile containing parameters for sexual stimulation device operation or the user's biometric information, stores the user's profile information, and outputs the user's profile information to the device controller 702. The device controller 702 adjusts the signals from the video analysis engine 701 based on the profile information from the control interface 703 and outputs the adjusted signals to a stimulation device 704 such that they are synchronized with the activity shown in the video. In an aspect of an embodiment, the parsed video information from the video analysis engine 701 is stored in a data storage device 705 for later retrieval and use.

Figure 8:
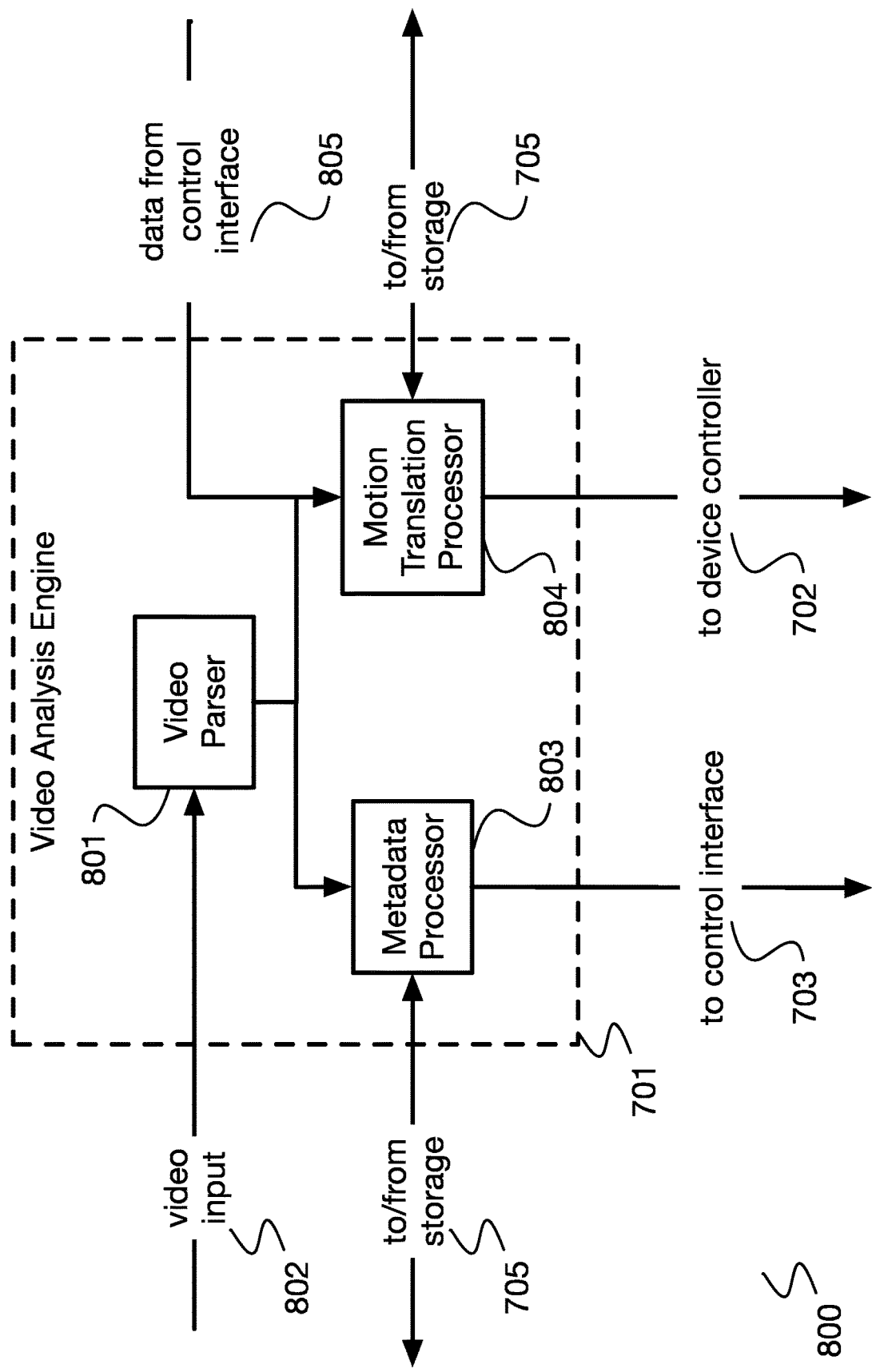
FIG. 8 is a block diagram of the video analysis engine aspect of an exemplary synchronized video control system for sexual stimulation devices.

FIG. 8 is a block diagram 800 the video analysis engine 701 aspect of an exemplary synchronized video control system for sexual stimulation devices. A video parser 801 receives video input 802, sends the video's metadata to a metadata processor 803, which checks to see if the metadata for that video already exists in the data storage device 705. If the metadata already exists, it is read from the data storage device 705 and sent out the control interface 703. If the metadata does not exist, it is formatted, written to the data storage device 705, and sent out to the control interface 703. Simultaneously, the video parser 801 sends the video content to the motion translation processor 804, which checks to see if the control signal data for that video already exists in the data storage device 705. If the control signal data already exists, it is read from the data storage device 705 and sent out the device controller 702. If the control signals do not exist, the motion translation processor 804 uses video processing algorithms and machine learning algorithms to detect sexual activity and to translate the motions in the video to control signals related to movement, pressure, and rhythm, and makes adjustments to the control signals in response to data from the control interface 805. The controls signals are then written to the data storage device 705 and sent out to the device controller 702. In an aspect of an embodiment, the actual video content may also be stored in the data storage device 705.

Figure 9:
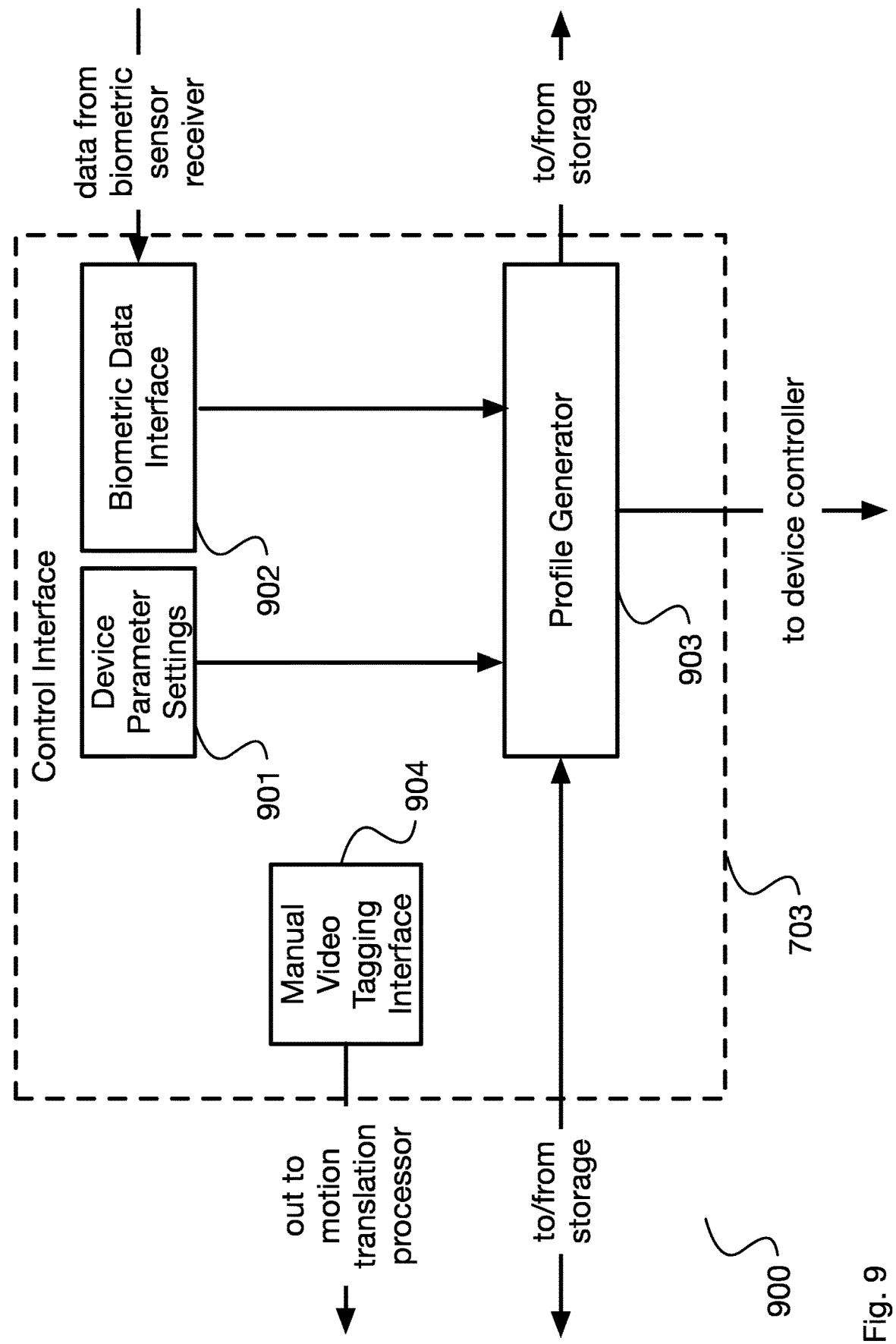
FIG. 9 is a block diagram of the control interface aspect of an exemplary synchronized video control system for sexual stimulation devices.

FIG. 9 is a block diagram 900 of the control interface 703 aspect of an exemplary synchronized video control system for sexual stimulation devices. The user can enter device parameter settings 901 to adjust operation of a compatible device. The user can further enter biometric data manually, or it may be obtained automatically by the biometric data interface 902 from biometric sensor receiver 1004 disclosed in FIG. 10. The parameters and biometric data are sent to a profile generator 903, which creates a profile for the user based on the various inputs. The profile information is saved to the storage device 705 and is sent to the device controller 702. The control interface may contain a manual video tagging interface 904, which allows the user to adjust the sensations received while viewing those videos.

Figure 10:
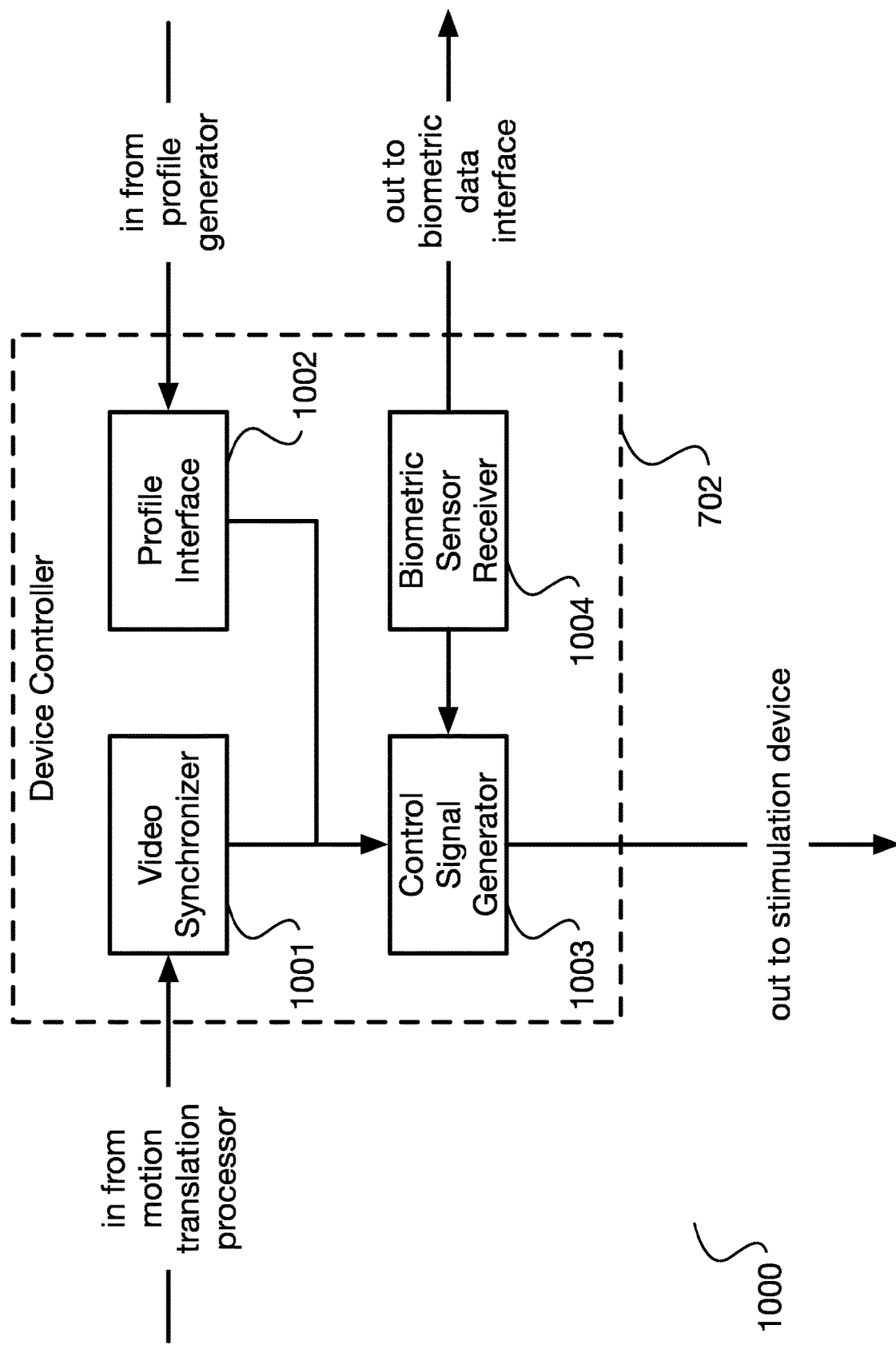
FIG. 10 is a block diagram of the device controller aspect of an exemplary synchronized video control system for sexual stimulation devices.

FIG. 10 is a block diagram 1000 of the device controller 702 aspect of an exemplary synchronized video control system for sexual stimulation devices. Control signals for the video being watched are received from the motion translation processor 804 into the video synchronizer 1001, which adjusts the timing of the signals to correspond with the video being watched. Parameters and biometric data are received into the profile interface 1002 from the profile generator 903. A control signal generator 1003 receives the outputs from both the video synchronizer 1001 and profile interface 1002 and adjusts the synchronized control signals based on the parameters and biometric data and sends out the adjusted control signal to the stimulation device 704. The device controller may also contain a biometric sensor receiver 1004 that could allow the capture of biometric data from wireless devices such as fitness trackers that monitor heart rate, blood pressure and breathing monitors, and even sensors in the stimulation device itself. The data captured through the biometric sensor receiver could be used for real time feedback to the control signal generator 1003 and for use in improving user experiences by enhancing the user's profile or improving the accuracy of video selection.

Figure 11:
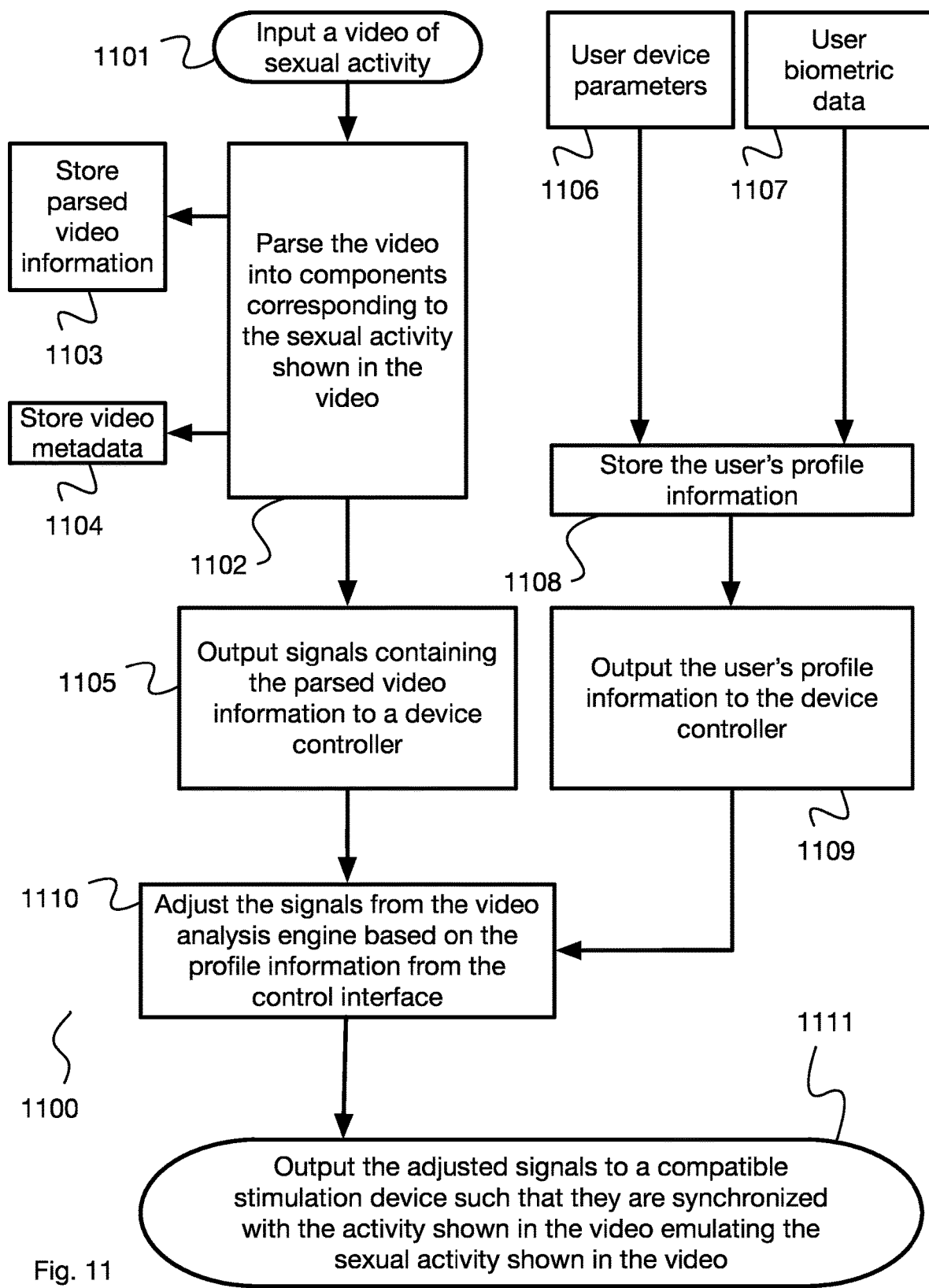
FIG. 11 is a flow diagram showing a method for an exemplary synchronized video control system for sexual stimulation devices.

FIG. 11 is a flow diagram showing a method 1100 for an exemplary synchronized video control system for sexual stimulation devices. According to this method, video of sexual activity would be input into a computer 1101. The computer, using machine learning algorithms, would parse the video into at least one component corresponding to the sexual activity shown in the video 1102. The parsed video information could be stored for later retrieval 1103 and any video metadata could also be stored for later retrieval 1104. Signals containing the parsed video information to a device controller would be output to a device controller 1105. Separately, the user would be allowed to enter a profile in a control interface containing at least parameters for adjusting compatible device operation 1106, and biometric data 1107, which would be stored 1108, and output to the device controller 1109. The signals from the parsed video would be adjusted based on the user's profile information 1110 and output to a compatible device, synchronized with the activity shown in the video, such that the compatible device would emulate the sexual activity shown in the video 1111.

Figure 12:
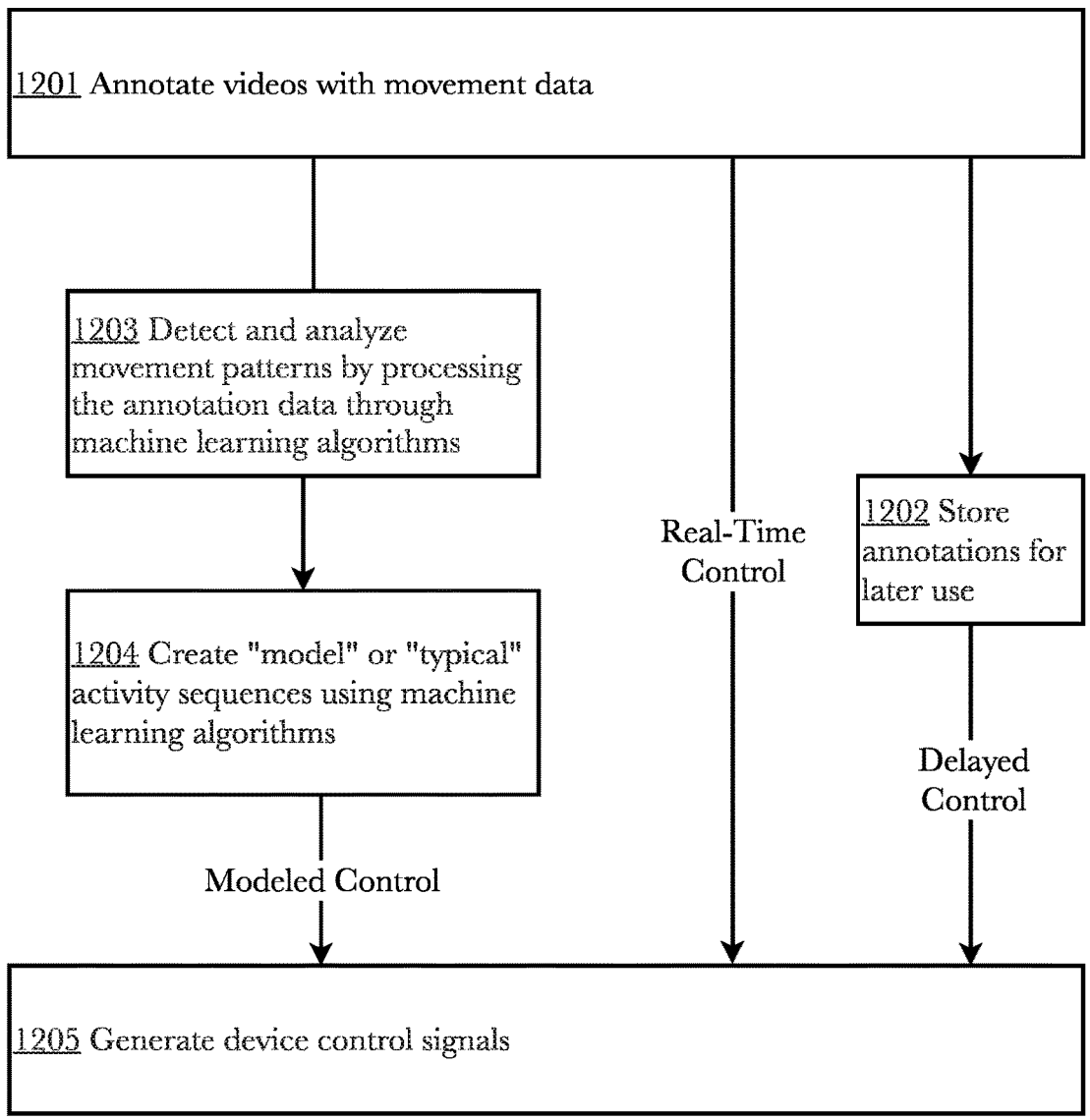
FIG. 12 is a flow diagram showing a method for using annotated video data to control a sexual stimulation device.

FIG. 12 is a flow diagram showing a method for using annotated video data to control a sexual stimulation device. In a first step, videos containing depictions of sexual activity are annotated (or tagged) with data regarding one or more movements shown in the videos 1201. The annotations are associated with playback times in the video, either as metadata incorporated into the video file or as separate files. The annotations (or tags) may be performed manually by a person watching the video or automatically by the video analysis engine 701.

The annotations may be used directly to generate device control signals 1205, such as real-time use wherein the device control signals are generated 1205 immediately or very soon after the annotations are created, or delayed use by storing the annotations for later use 1202 and generating device control signals 1205 from the stored annotations. In this use, the annotations will typically be used to generate control signals for a particular video for which the annotations were made. A single such annotation may be used or some combination of annotations for the same video (e.g., averaging of multiple annotations).

Alternatively, the annotations may be processed through machine learning algorithms to create models of movement patterns and sequences commonly associated with certain videos, or certain sexual activities, persons, etc. In this use, annotations from a plurality of different videos will typically be used. The annotations are processed through a first set of machine learning algorithms to detect and analyze movement patterns typical of certain sexual activities 1203. This first set of machine learning algorithms may use techniques such as clustering to group together similar types of movement patterns. The movement pattern data are then processed through a second set of machine learning algorithms to determine sequencing information 1204 such as how long a pattern is typically held and the probabilities of changing to different patterns after the current pattern. The sequencing information is used to create predictive models of typical or expected sequences of movement patterns, which mimic frequently-seen depictions of sexual activity in the annotated data. The data from these models may then be used to generate device control signals 1205 representing movement patterns and sequences in common sexual activities.

Figure 13:
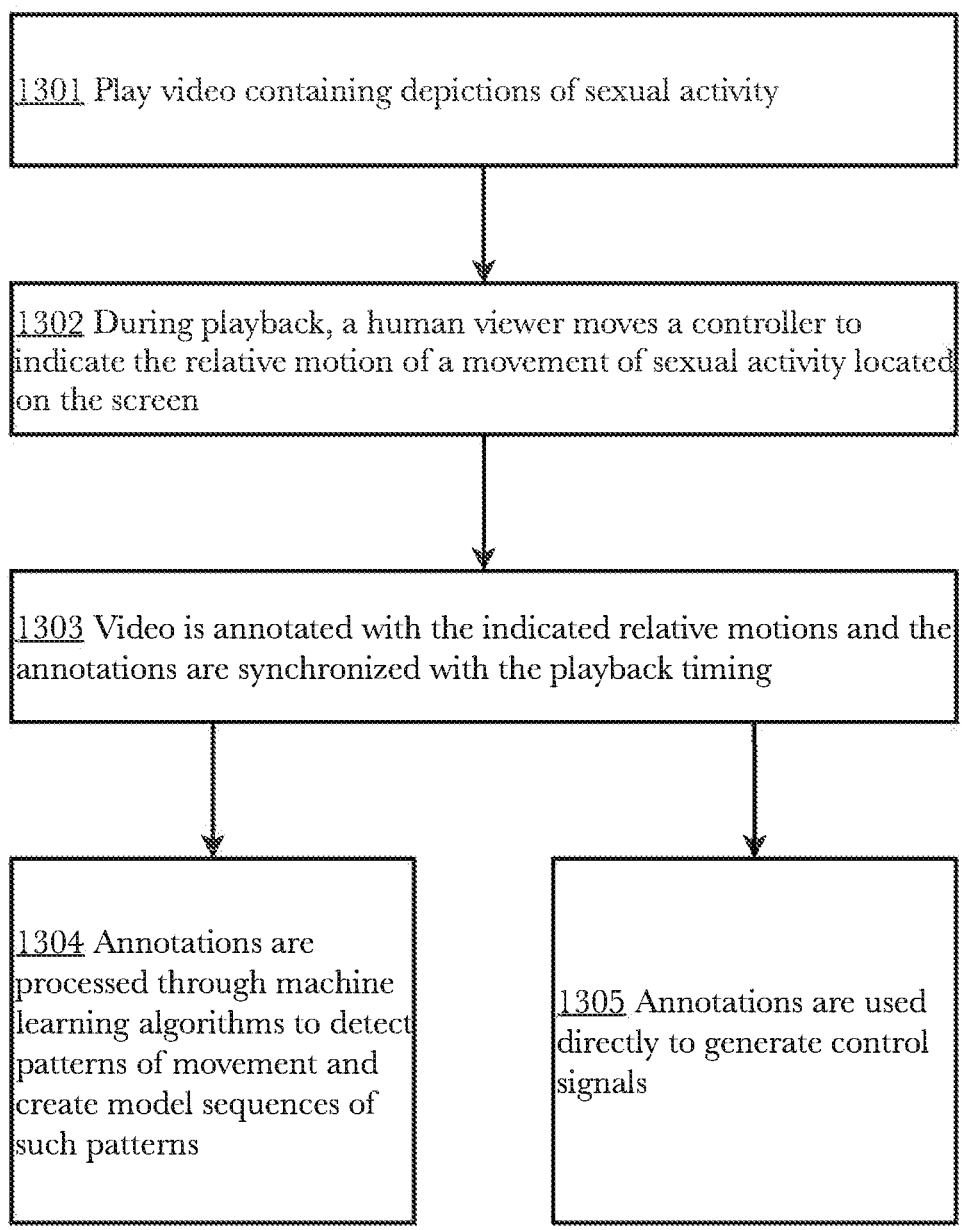
FIG. 13 is a flow diagram showing a method for manual annotation of videos containing depictions of sexual activity.

FIG. 13 is a flow diagram showing a method for manual annotation of videos containing depictions of sexual activity. In a first step, a video is played which contains depictions of sexual activity 1301. During playback, a human viewer moves a controller to indicate the relative motion of a movement of sexual activity located on the screen. The controller may be any device that allows the viewer to input a motion associated with a movement of sexual activity in the video being viewed by the viewer 1302. Ideally, the controller will allow the viewer to simply imitate the motion by mimicking the motion(s) seen in the video (e.g., moving the viewer's hand back and forth) rather than programming in the motion(s) (e.g., by entering a number associated with the motion). The controller may be virtual (e.g., an on-screen slider bar, an on-screen virtual joystick, gestures made in front of a gesture-recognition camera), or the controller may be a physical device (e.g., a physical slider, joystick, wand, mobile phone with an accelerometer, etc.). The controller may allow for linear motions, two-dimensional motions, or three-dimensional motions, and may also allow for rotation or tilting. As the human viewer moves the controller in synchronicity with the movements depicted in the video, annotation data are created that are associated with video playback times 1303. As a simple example, a reciprocal motion depicted in the video may be annotated as tuples, with a series of time stamps representing the video playback time, each associated with a value indicating the relative location of the linear motion in the video at that time. The annotations may be incorporated into the video file as metadata or stored as separate data files. Where the annotations will be used to generate device control data for a particular video, the annotation will typically be associated with the video in some manner. However, where the annotations are to be used as input to machine learning algorithms for generation of models of sexual activity, the annotations may be disassociated with the video from which they are derived. The annotations may then be used to generate control signals 1305, or may be processed through machine learning algorithms to detect patterns of movement and create model sequences of such patterns mimicking the movements of sexual activity associated with certain concepts (e.g., frequently-seen movements represented in a certain type of video, or certain sexual activities, or associated with certain actors and actresses, etc.) 1304.

Figure 14:
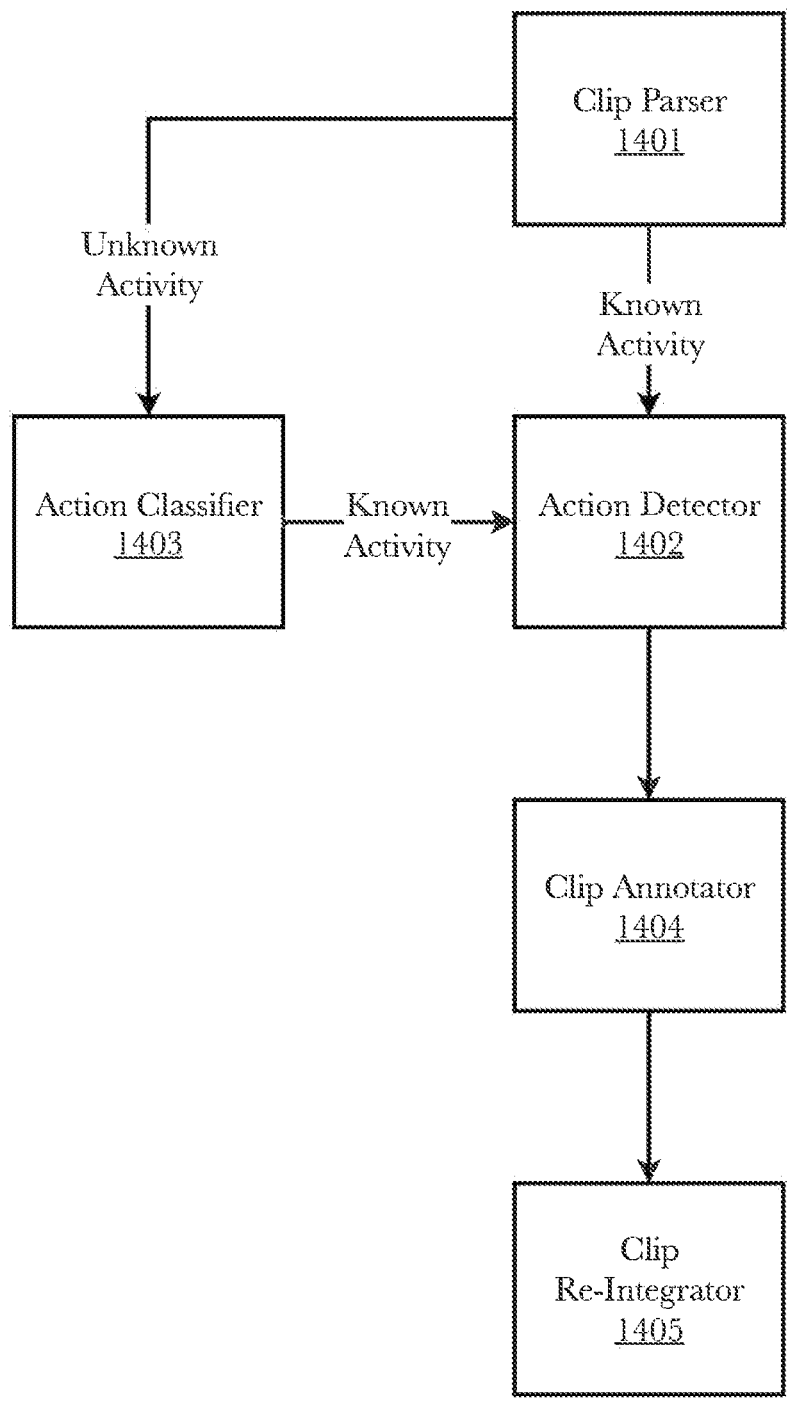
FIG. 14 is a block diagram showing an exemplary system architecture for automated annotation of videos containing depictions of sexual activity.

FIG. 14 is a block diagram showing an exemplary system architecture for automated annotation of videos containing depictions of sexual activity. This exemplary system architecture provides more detail regarding the operation of the video analysis engine 701. In some embodiments, this exemplary system architecture, or a similar one, may be incorporated into the video analysis engine 701 as a component, or as a component of the video parser 801, the metadata processor 803, or the motion translation processor 804. In some embodiments, this system architecture may be distributed among, or substitute for, one or more components of the video analysis engine 701. In some embodiments, this system architecture or it components may exist separately from, but remain accessible to, the video analysis engine 701.

In this exemplary embodiment, a clip parser 1401 parses (i.e., breaks breaks or segments) a video into smaller clips to reduce the scale of the video processing by the machine learning algorithms (i.e., reduces the video to more easily manageable smaller clips of a larger video). Depending on the size of the video, available processing power, and the machine learning algorithm to be used, the clip parser 1401 may reduce the video to any size ranging from the entire video to frame-by-frame clips of the video. Where a video is annotated with known activities (e.g., where the video or segments of the video have been annotated with an indication of the type of activity that is contained therein), the clip parser 1401 may parse the video into clips corresponding to the length of the known activity, as indicated by the annotations. In such cases, the clip parser 1401 forwards the clips of known activity directly to an action detector 1402. Where the video contains depictions of unknown activities, the clip parser will parse the video into uniform sizes (e.g., frame-by-frame, or a certain number of frames representing several seconds or minutes of video), and send the video to an action classifier 1403, which classifies the activities in the video before sending them an known activities to the action detector 1402.

The action classifier 1403 comprises one or more machine learning algorithms that have been trained to classify human actions. Classification of human action is a simpler activity than human action detection. Human action classification involves identification of human objects in the video and some classification of the activity being demonstrated by the human objects (e.g., standing, walking, running, jumping, etc.). Classification does not require a determination of when the action starts, where in the frame the action occurs, or the relative motion of the action; it simply requires that an object in the video be recognized as a person and that the activity of that person be identified.

The action detector 1402 received videos of known sexual activity (i.e., those that have already been classified either manually or using machine learning algorithms), and detects when the action starts, where in the frame the action occurs, or the relative motion of the action. Because the activity in the video is already known, machine learning algorithms may be employed which have been specially-trained for the type of activity depicted in the video. Action detection involves first segmenting the video into objects and backgrounds, identifying human objects in each frame of video, and tracking the movement of those human objects across video frames.

Both action classification and action detection rely on color-based processing of pixels in each frame of the video. Most videos currently available, whether or not depicting sexual activity, are two-dimensional (2D) videos containing color information only (e.g., the RGB color model), from which depth information must be inferred. The additional of depth sensors allows the addition of depth information to the video data (e.g., RGBD color/depth model), which improves human pose estimation but requires specialized sensors that must be used at the time of filming. Due to the processing-intensive nature of analyzing videos using machine learning algorithms, some simplification techniques may be used to reduce the computing power required and/or speed up the processing time. For example, facial recognition algorithms have become widely used, fairly accurate, and can be implemented on computing devices with modest processing power. Thus, for videos where fellatio is known to be the primary sexual activity, facial recognition algorithms may be used as the machine learning component to track the relative position and orientation of the face in the video to indicate the movement component of sexual activity. This greatly reduces the amount of computing power required relative to videos containing unknown sexual activity and/or where whole body human activity must be classified and detected. As there is a limited range of possible sexual activity, and certain sexual activities are more common than others, specially-trained machine learning algorithms can be employed for given types of sexual activity to improve action classification and action detection times and accuracy.

For both action classification and action detection, a variety of machine learning algorithms may be used. For example, as noted above, a convolutional neural network (CNN) may be applied to perform segmentation of each video frame. Other machine learning algorithms or combinations of machine learning algorithms may be employed. For example, a CNN may be employed to extract the features in the video, followed by a long short-term memory (LSTM) algorithm to evaluate the temporal relationships between features. In another example, a three-dimensional CNN (3D CNN) may be employed which can directly create hierarchical representations of spatial and temporal relationships, thus obviating the need to processing through an LSTM. In another example, a two-stream CNN may be used, wherein the first stream of input into the CNN is a set of temporal relationships that are established by a pre-determined set of features, and the second stream is frames from the video. Action classification and/or action detection can be performed by averaging the predictions of the CNN, or by using the output of the CNN for each frame of the video as input to a 3D CNN. Many other variations are possible, and while CNNs are particularly suitable for video processing, other types of machine learning algorithms may be employed.

The clip annotator 1404 associates each video clip with action detection data synchronized with the playback times (or frames) of the video clip, and the clip re-integrator 1405 combines the clips back into the original video received by the clip parser 1401. The annotated video, or just the annotations data from the video, may then be used to generate device control data or may be further processed to extract models of typical sexual activity prior to generating device control data.

Figure 19:
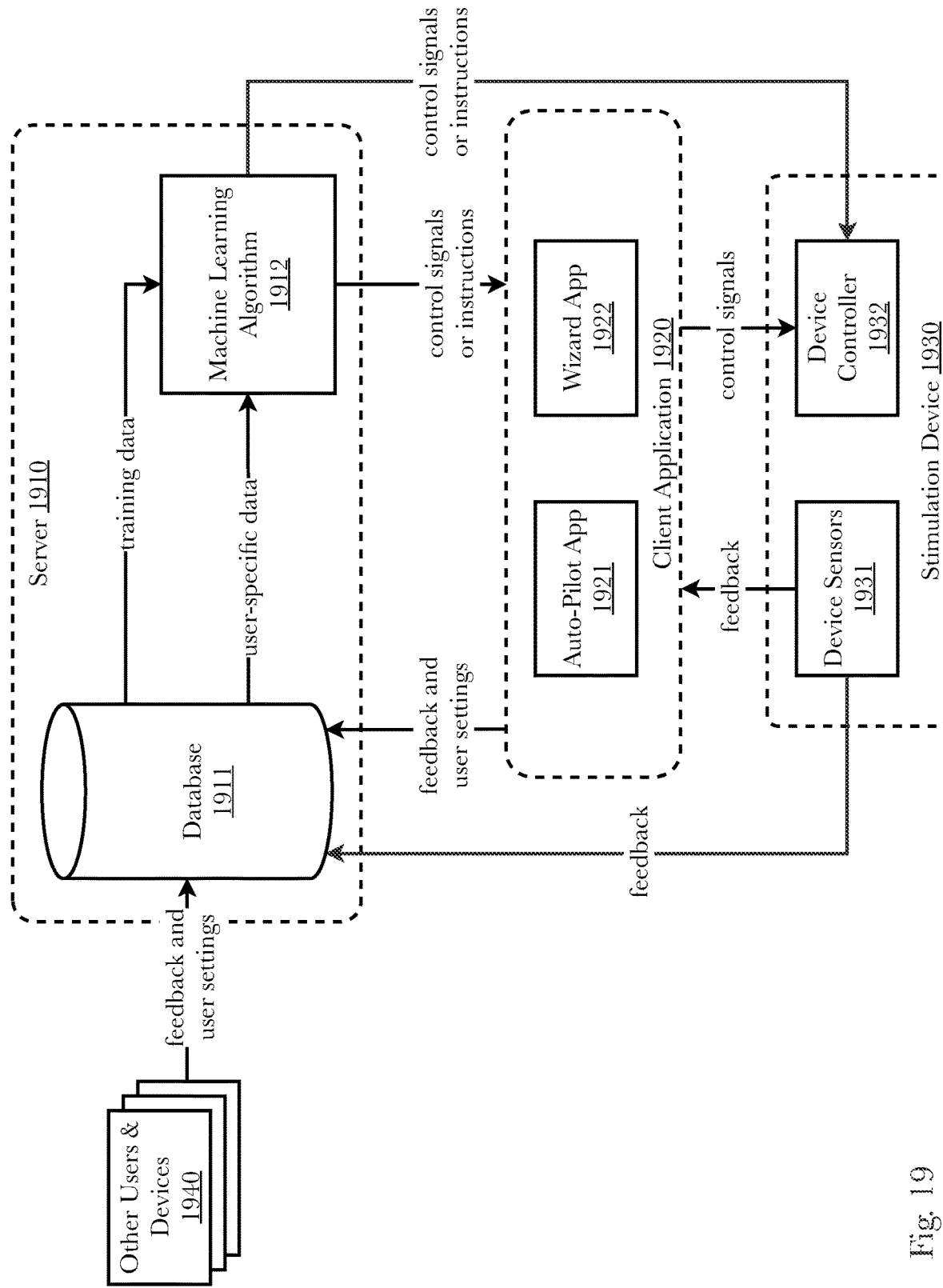
FIG. 19 is an exemplary system architecture diagram for a system for automated control of sexual stimulation devices.

FIG. 19 is an exemplary system architecture diagram for a system for automated control of sexual stimulation devices. In this embodiment, the system comprises a server 1910, a client application 1920, a stimulation device 1930, and data from other users and devices 1940.

The server may be a network-connected, cloud-based, or local server 1910, and comprises a database 1911 for storage of usage data comprising user profiles, user/device feedback, and user/device settings, and a machine learning algorithm 1912 for analysis of the data stored in the database 1911 for generation of automated control signals or instructions. The machine learning algorithm 1912 is trained on the data to identify patterns within the usage data wherein certain characteristics of user profiles are correlated with satisfaction or dissatisfaction with certain aspects of stimulation profiles such as tempo, location, intensity, pressure, and patterns. The usage data may contain user profiles comprising personal information about the user such as age, sex, height, weight, and fitness level; sexual preferences such as straight, gay, bi-sexual, etc.; stimulation preferences such as stimulation tempo/speed, stimulation intensity, location of stimulation, patterns of stimulation; and feedback information such as user ratings, heartrate data from sensors, moisture data from sensors, etc. After training, when a user profile (or one or more characteristics from a user profile) is input into the machine learning algorithm 1912, the machine learning algorithm 1912 generates one or more stimulation profiles (comprising one or more stimulation aspects such as tempo/speed, stimulation intensity, location of stimulation, patterns of stimulation) that correspond with satisfaction based on the characteristics of the user profile input and outputs control signals (or instructions for generating control signals) for stimulation profiles that correspond with satisfaction based on the characteristics of the user profile input. The machine learning algorithm 1912 may periodically or continuously be re-trained based on new data from the client application 1920 (such as, but not limited to, feedback and other changes to the user's profile) and the data from other users and devices 1940 being similarly stored and processed. It should be noted that, while a machine learning algorithm is used in embodiment, the system is not necessarily limited to use of machine learning algorithms and other processes for analysis of the data may be used, including but not limited to modeling and statistical calculations.

The system of this embodiment further comprises a client application 1920, which is a software application operating on a computing device, which may be of any type including but not limited to a desktop computer, tablet, mobile phone, or even a cloud-based server accessible via a web browser. The client application 1920 acts as an interface between the stimulation device 1930 and the machine learning algorithm 1912, relaying feedback from the device to the server 1910 and relaying control signals (or translating instructions into control signals) to the device controller 1932 of the stimulation device 1930. The client application may comprise one or more applications such as the auto-pilot application 1921 and the wizard application 1922. Depending on configuration, the client application may further act as a user interface for operation of, and/or changing settings of, the stimulation device 1930.

In this embodiment, the auto-pilot application 1921 automatically controls the stimulation device 1930 for the user with little or no input from the user. The auto-pilot application stores and retrieves user-specific data for the user of the stimulation device 1930 from a user profile entered into the client application 1920, from sensors on the device (e.g., tumescence sensors, heartrate sensors or heartrate signal receivers, pressure sensors, etc.), and from user interactions with the client application 1920 via a user interface. The data gathered about the user may include such as, but not limited to, where the user prefers to be stimulated, what tempo or speed of stimulation the user prefers, what stimulation patterns the user prefers, and general preferences such as quick stimulation to orgasm, delayed orgasms, multiple edging before orgasm, etc.

The auto-pilot application 1921 provides the user-specific data to the server 1910 and requests control signals (or instructions for control signals) for a stimulation profile that is customized to the user based on the user data. The user-specific data is processed through the trained machine learning algorithm 1912, which selects appropriate stimulation routines and provides control signals or instructions back to the client application for operation of the stimulation device 1930. In some embodiments the control signals or instructions may be sent directly from the machine learning algorithm 1912 directly to the device controller 1932 of the stimulation device 1930. The client application 1920 may be configured to periodically or continuously send updated user-specific data to the server 1910 for processing by the machine learning algorithm 1912 to generate modified or updated control signals or instructions, thus changing and evolving the automated operation of the device based on changed or updated information from the device sensors 1931, client application 1920, or updating/retraining of the machine learning algorithm 1912 based on this user's data and the data from other users and devices 1940 being similarly stored and processed.

In this embodiment, the set-up wizard application 1922 builds an initial personalized stimulation profile from a series of ratings by the user of test stimulations. Completion of the set-up wizard application 1922 process accelerates customization of a stimulation profile for the user by providing a base set of ratings of various aspects of stimulation which can then be processed through the trained machine learning algorithm 1912 to automatically control the stimulation device 1930, as further shown in FIG. 20. After completion of the set-up wizard application 1922, stimulation profiles for the user may continue to evolve from new user-specific data as described above. In some embodiments, the set-up wizard application 1922 and auto-pilot application 1921 operate independently from one another, while in other in other embodiments the set-up wizard application 1922 is the first step in the automated control process, followed by further automation by the auto-pilot application 1921.

In some embodiments, the client application 1920 may exist as an application on a user's mobile phone and may interface with the stimulation device 1930 via a local network (e.g., WiFi, Bluetooth, etc.). In other embodiments, the client application 1920 may exist as an application on the server 1920 accessible via a user account also residing on the server. In other embodiments, certain components of the server 1910 and client application 1920 may reside on tablet computer or other mobile device, or on the stimulation device 1930 itself (e.g., a copy of the trained machine learning algorithm could reside on a smartphone such that automated generation of control signals can be accomplished without access to the server). In some embodiments, the client application 1920 and/or server components will be integrated into the stimulation device 1930 (e.g., stored in a memory and operable on the device controller 1932) instead of residing on a separate computing device.

The stimulation device 1930 may be any device configured to provide sexual stimulation by any variety of means, including but not limited to, linear stroking, vibration, rotation, heat, electrical stimulation, or combinations of the above. Device sensors 1931 may be any sensor on the device capable of providing data regarding an aspect of sexual arousal, including but not limited to, heartrate sensors, moisture sensors, tumescence sensors, pressure sensors, strain gauges, and length/distance sensors. Further, the device sensors 1931 include devices capable of receiving sensor data from external sensors (e.g., wearable fitness devices that record heart rates) via WiFi, Bluetooth, or other networking technologies. The device controller 1932 is a device capable of operating the stimulation device based on control signals received. The device controller 1932 may be a simple power relay switching device that receives low-powered signals and outputs corresponding power to motors, vibrators, etc., or may be a computing device with a memory, processor, and storage. In the latter case, the device controller 1932 may be configured to receive instructions to generate control signals and generate the control signals, itself. Further, in some embodiments, aspects of the client application and/or machine learning algorithm 1912 may be incorporated into the device controller 1932.

Detailed Description of Exemplary Aspects

FIG. 1 shows the internal workings of an exemplary sexual stimulation device 100. The compatible device is a small handheld unit powered by a low voltage, external direct current (DC) power source. Inside the device is a metal framework 101 to which the mechanical parts of the device are attached. Attached to the metal framework 101 is a small DC motor 102 with a motor shaft 103, which drives the stimulation mechanism. A screw shaft 104 is affixed to the motor shaft 103 of the DC motor 102, such that the screw shaft 104 rotates as the motor shaft 103 of the DC motor 102 rotates. The polarity of voltage to the DC motor 102 may be reversed so that the motor shaft 103 of the DC motor 102 rotates both clockwise and counter-clockwise. A flex coupling 105 between the motor shaft 103 of the DC motor 102 and screw shaft 104 compensates for any misalignment between the two during operation. A screw collar 106 is placed around the screw shaft 104 and attached to a bracket 107, which is held in a particular orientation by guide rods 108, such that the screw collar 106 and bracket 107 travel in a linear motion as the screw shaft 104 is turned. Affixed to the bracket 107 is a gripper 109, which travels in a linear motion along with the bracket 107. A hole 110 in the metal framework 101, allows for the insertion of a flexible sleeve as shown in FIG. 2.

Figure 2:
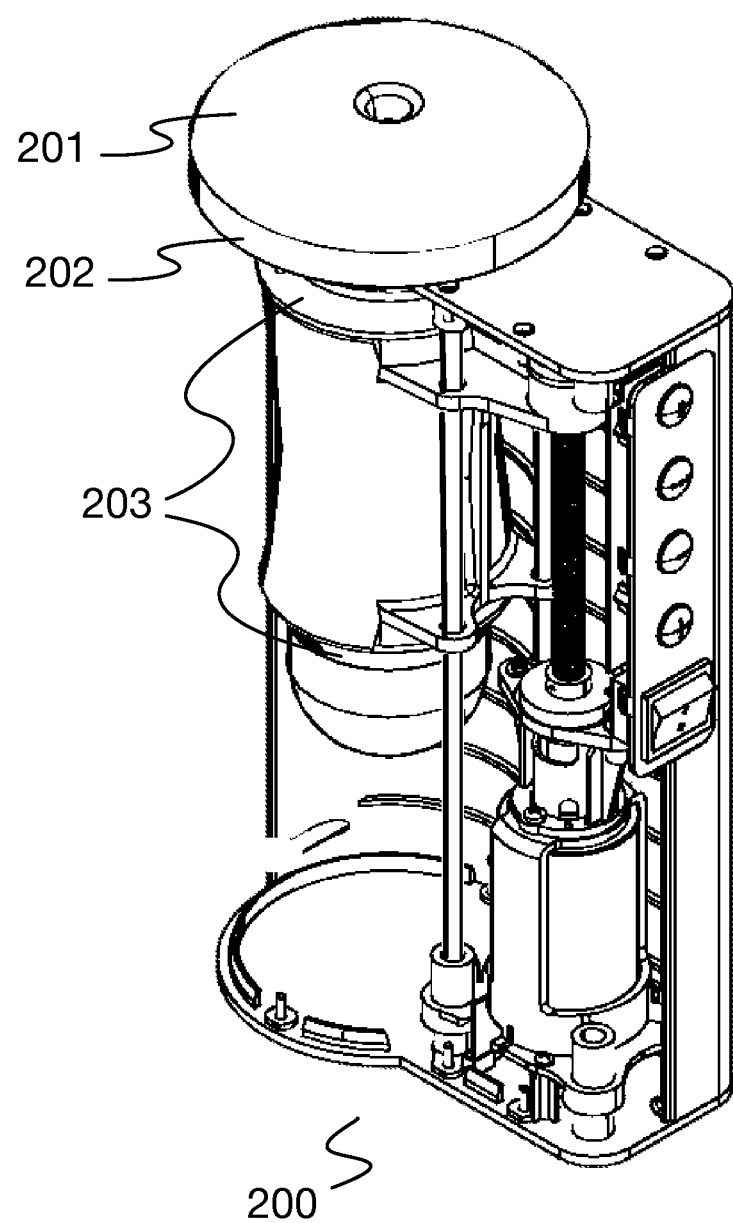
FIG. 2 shows additional components of the internal workings of an exemplary sexual stimulation device.

FIG. 2 shows additional components of the internal workings of an exemplary sexual stimulation device 200. A flexible sleeve 201 made of either thermoplastic elastomer (TPE) or thermoplastic rubber (TPR) is inserted through a large hole 109 in the metal framework 101 and through gripper 108. Sleeve 201 is prevented from accidentally slipping into device 200 by a ridge 202 at the open end of sleeve 201 and is held in the proper position by ridges 203 at both ends of gripper 108. During operation, gripper 108 slides in a reciprocal linear motion 201 providing pressure and motion against the penis inside the sleeve 201 in a manner similar to sexual intercourse or manual masturbation. Depending on the configuration, gripper 108 may either grip sleeve 201 and move sleeve 201 along the penis, or it may slide along the outside of sleeve 201, not moving the sleeve relative to the penis. Also depending on configuration, gripper 108 may be made of rigid, semi-rigid, or compliant materials, and other shapes might be used (e.g., partial tube, ring, half-ring, multiple rings, loops of wire) and may contain rollers or bearings to increase stimulation and reduce friction against the flexible sleeve 201.

Figure 3:
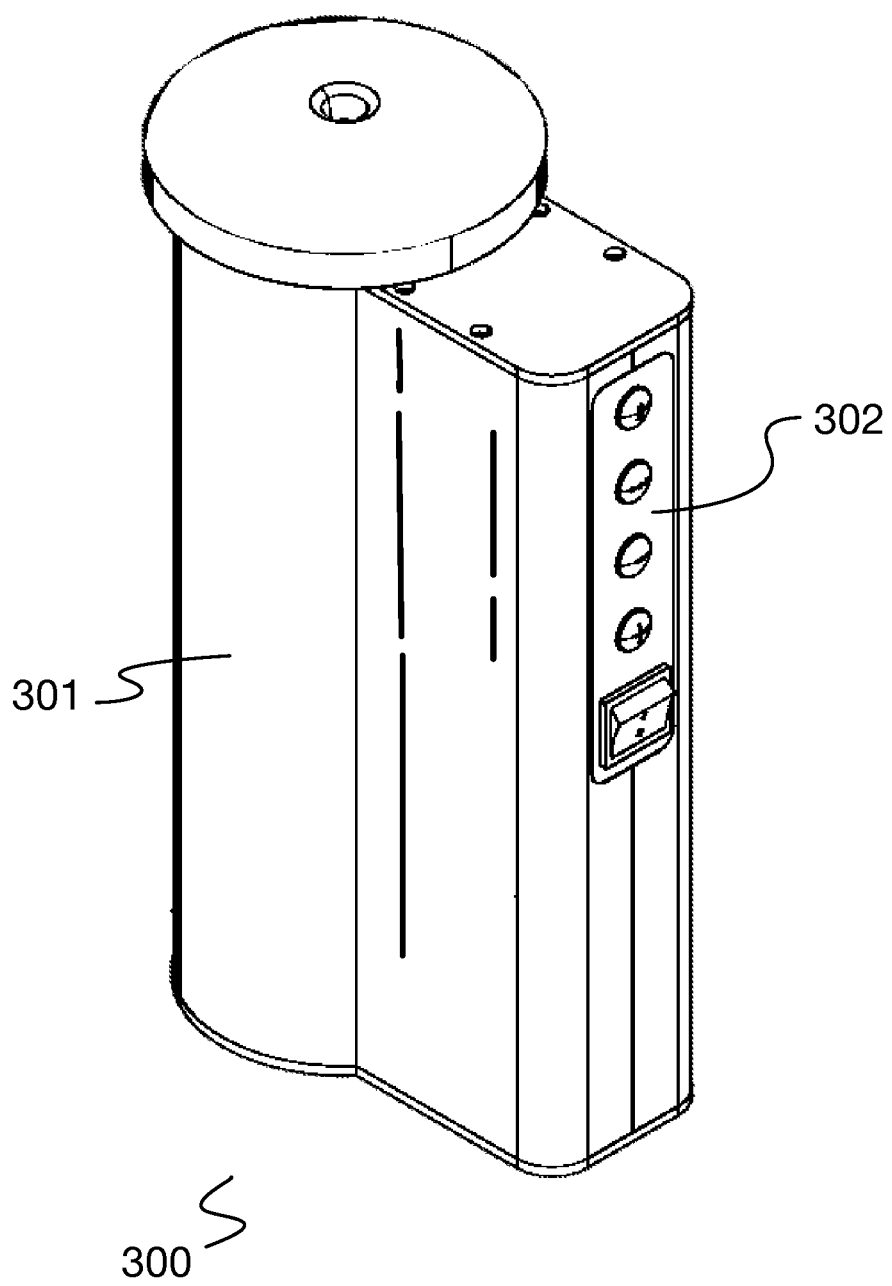
FIG. 3 shows the external structure of an exemplary sexual stimulation device.

FIG. 3 shows the external structure 300 of an exemplary sexual stimulation device. The housing 301 of the device is made of plastic and is attached to the metal framework in such a way as to provide additional support and structure to the device. User controls 302 in the form of buttons and switches and their associated electronics are built into the housing. The housing has an opening at one end corresponding to the opening 109 in the metal framework 101, into which the flexible sleeve 201 is inserted. The penis is inserted into the sleeve 201 at the end of the device and is stimulated by the reciprocal linear motion of the gripper 108 inside the device. The user controls the speed, pattern, and location of stimulation using the controls 302 on the outside of the housing 301.

Figure 4:
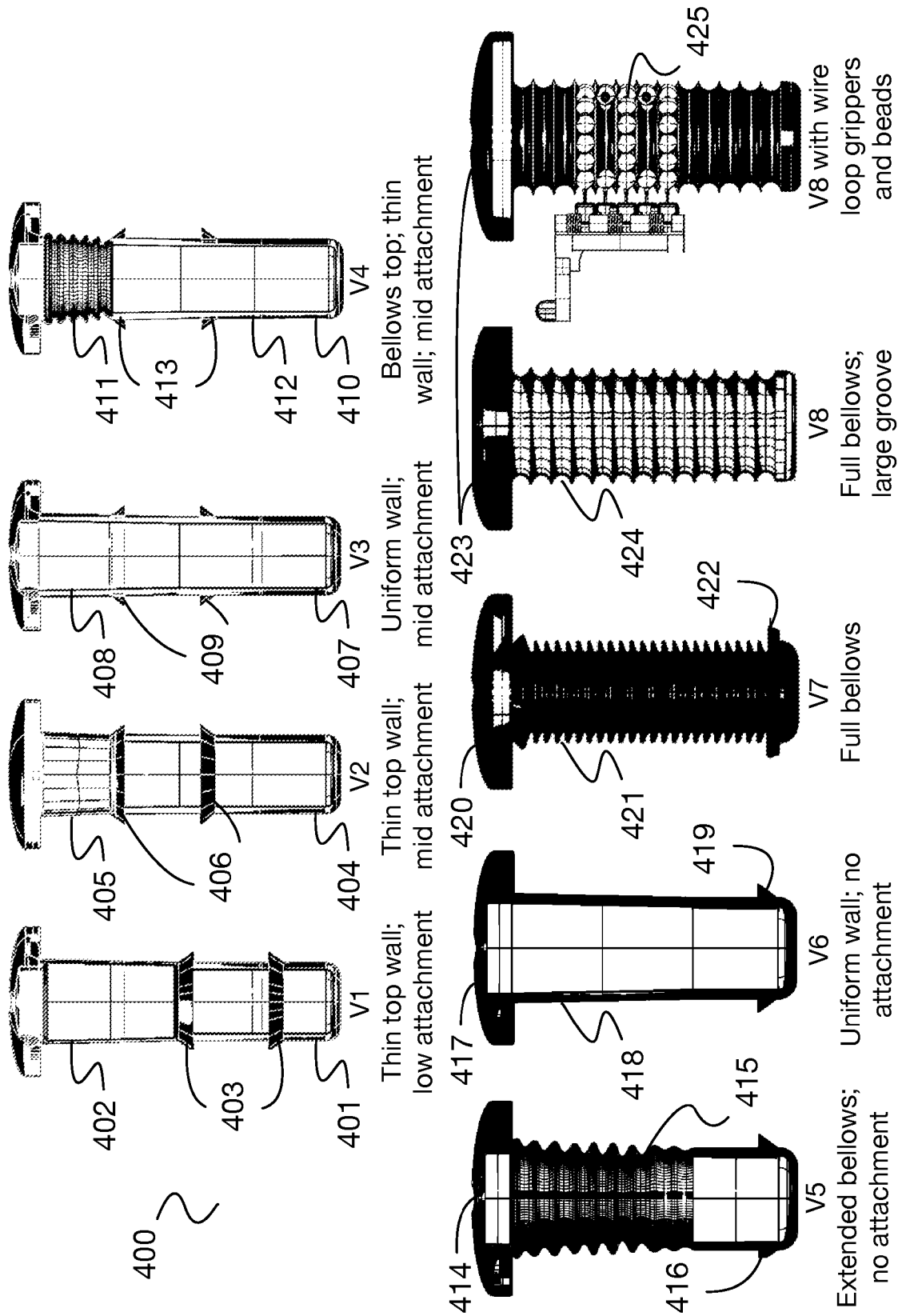
FIG. 4 shows exemplary variations of the sleeve and gripper aspects of an exemplary sexual stimulation device.

FIG. 4 shows exemplary variations 400 of the sleeve 201 and gripper 108 aspects of an exemplary sexual stimulation device. As noted above, different configurations of the sleeve 201 and gripper 108 are possible to allow optimal fit and sensation for penises of different lengths and girths, and to allow the user a choice of pressure, gripper location, and sensation. Sleeve variant one 401 has a thin top wall 402 with a low point of attachment 403 to the gripper 108. Sleeve variant two 404 has a thin top wall 405 with a middle point of attachment 406 to the gripper 108. Sleeve variant three 407 has a uniform wall thickness 408 with a middle point of attachment 409 to the gripper 108. Sleeve variant four 410 has a bellows top 411, a thin wall 412, and a middle point of attachment 413. Sleeve variant five 414 has an extended bellows 415 and no attachment to the gripper 108 other than a stopper at the end 416, allowing the gripper 108 to slide along the outside of the sleeve 414. Sleeve variant six 417 has a uniform wall thickness 418 and no attachment to the gripper 108 other than a stopper at the end 419, allowing the gripper 108 to slide along the outside of the sleeve 417. Sleeve variant seven 420 has a full bellows design 421 and no attachment to the gripper 108 other than a stopper at the end 422, allowing the gripper 108 to slide along the outside of the sleeve 420. Sleeve variant eight 423 has a full bellows design with large grooves 424 into which fits a gripper made of wire loops with beads attached 425.

Figure 5:
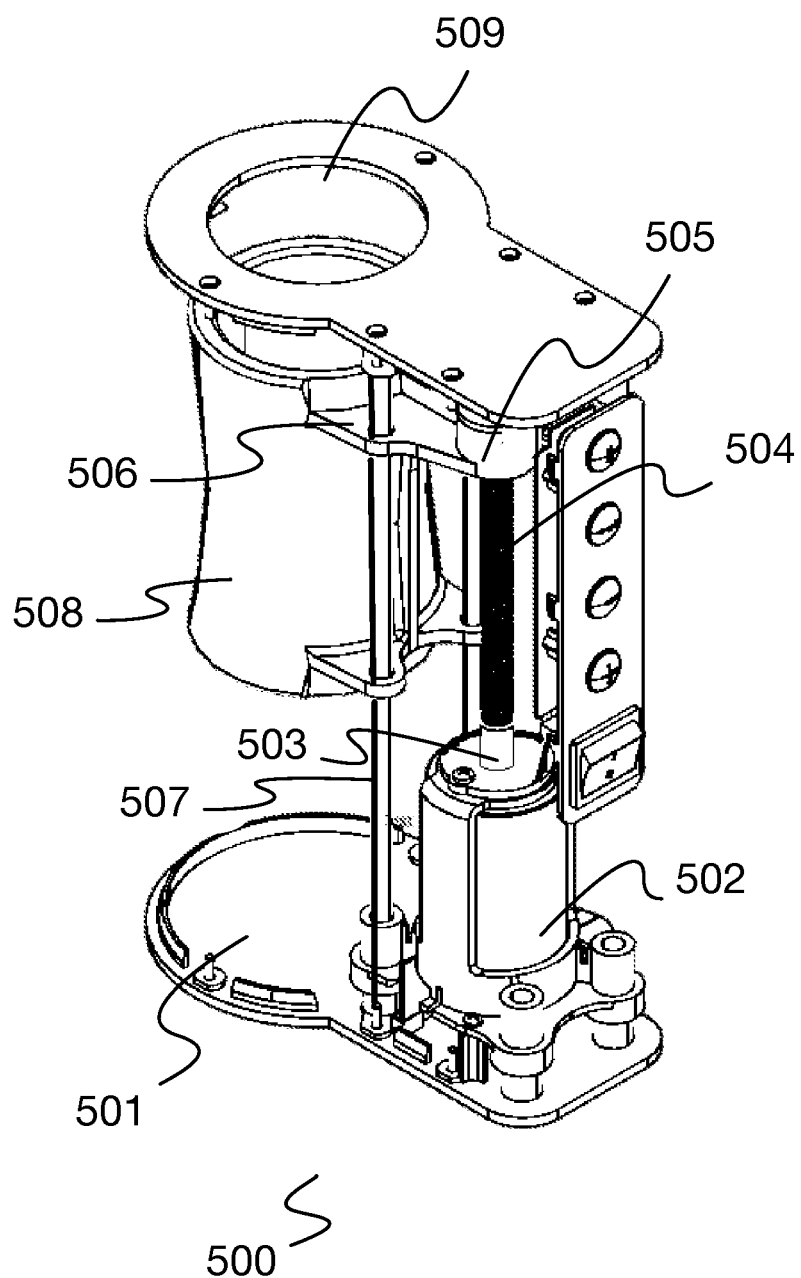
FIG. 5 shows the internal workings of an exemplary sexual stimulation device.
Figure 6:
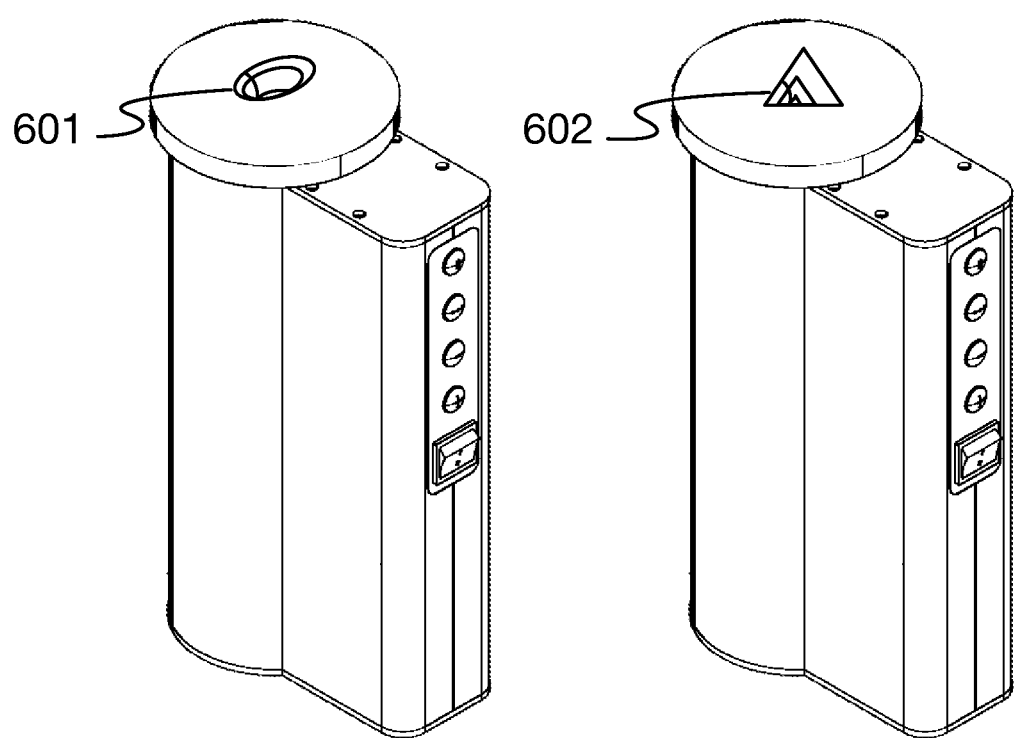
FIG. 6 shows additional exemplary aspects of an exemplary sexual stimulation device.

FIG. 5 shows the internal workings of an exemplary sexual stimulation device 500. The compatible device is a small handheld unit powered by a low voltage, external direct current (DC) power source. Inside the device is a metal framework 501 to which the mechanical parts of the device are attached. Attached to the metal framework 501 is a small DC motor 502 with a motor shaft 503, which drives the stimulation mechanism. A screw shaft 504 is affixed directly to the motor shaft 503 of the DC motor 502, such that the screw shaft 504 rotates as the motor shaft 503 of the DC motor 502 rotates. The polarity of voltage to the DC motor 502 may be reversed so that the motor shaft 503 of the DC motor 502 rotates both clockwise and counter-clockwise. In this embodiment, the flex coupling 105 has been eliminated, allowing the device to be constructed in a more compact form, approximately 2 cm shorter in overall length. A screw collar 505 is placed around the screw shaft 504 and attached to a bracket 506, which is held in a particular orientation by guide rods 507, such that the screw collar 505 and bracket 506 travel in a linear motion as the screw shaft 504 is turned. Affixed to the bracket 506 is a gripper 508, which travels in a linear motion along with the bracket 506. A hole 509 in the metal framework 501, allows for the insertion of a flexible sleeve 201 as previously shown in FIG. 2. FIG. 6 shows additional exemplary variations 600 of the sleeve aspect of an exemplary sexual stimulation device as set forth in another preferred embodiment. In this embodiment, the opening in the sleeve may be other than circular. For example, the opening may be elliptical in shape 601 or triangular in shape 602.

FIG. 6 shows additional exemplary variations of the aspects of an exemplary sexual stimulation device.

Figure 15:
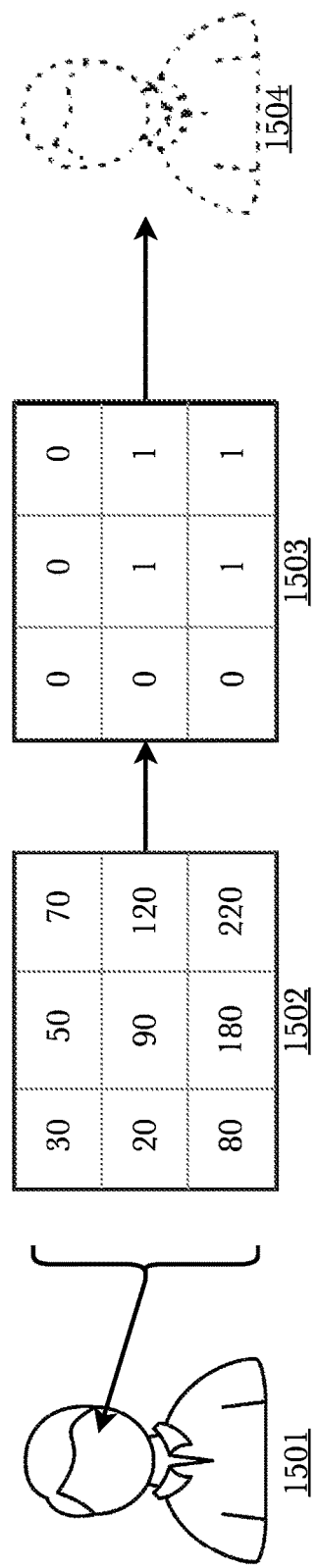
FIG. 15 (PRIOR ART) is a diagram describing the use of the local binary pattern (LBP) algorithm to extract the textural structure of an image for use in object detection.

FIG. 15 (PRIOR ART) is a diagram describing the use of the local binary pattern (LBP) algorithm to extract the textural structure of an image for use in object detection.

There are a wide variety of algorithms for extracting data from images and/or video (which is a series of images) for object recognition within the image. The local binary pattern (LBP) algorithm is one of the simplest and easiest to understand and is therefore used here to demonstrate in general terms how image data is processed to extract certain information. All digital images are composed of pixels, each of which represents the smallest area of viewable information in the image (i.e., each pixel is a "dot" in the image). Each pixel contains information about the color that the dot represents, and the color of the pixel may be either black and white, grayscale, or colored. The representation of the color may be in any number of standard formats (also called color models), with the hexadecimal (HEX), red, green, blue (RBG), and cyan, magenta, yellow, key/black (CMYK) being three of the most common. In this simplified example, the original image 1501 is in 256-bit grayscale, meaning that each pixel in the original image 1501 has a grayscale value of 0-255. The LBP algorithm is applied to each pixel in the original image 1501 by selecting a pixel and comparing the value of that pixel to the value of each surrounding pixel, as shown in the first table of values 1502, in which the selected pixel from the original image 1501 has a value of 90, and the values of the surrounding pixels from top left and going clockwise are 30, 50, 70, 120, 220, 180, 80, and 20. In a next step of the LBP algorithm, for each of the pixels in the first table 1502 is assigned a binary (zero or one) value in a second table 1503, wherein a zero is assigned if the value of the pixel is less than the value of the selected (i.e., center) pixel, and a one is assigned if the value of the pixel is equal to or greater than the value of the selected (i.e., center) pixel. The resulting values are shown in the second table 1503, wherein the pixels with values of 90, 120, 220, and 180 have been assigned a binary value of one, and all of the other pixels have been assigned a value of zero. The values of each of the pixels in the second table 1503 surrounding the selected (i.e., center) pixel are concatenated together in a clockwise manner starting from the top left, resulting in this case in the binary number 00011100. This binary number is then converted back to a decimal number, in this case 28, and this decimal number is substituted in for the value of the selected pixel in the original image 1501, representing a 256-bit grayscale value for the local area in which the selected pixel resides. This process is repeated for all pixels in the original image 1501, resulting in a texturized image 1504 wherein each pixel represents the "texture" of the surrounding pixels from the original image 1501. Many different processing methods can be used on the texturized image to identify features and objects in the texturized image, such division of the image into blocks and extracting histograms of each block and running the histograms through machine learning algorithms that have been trained to identify features from similar histograms from similar images.

Figure 16:
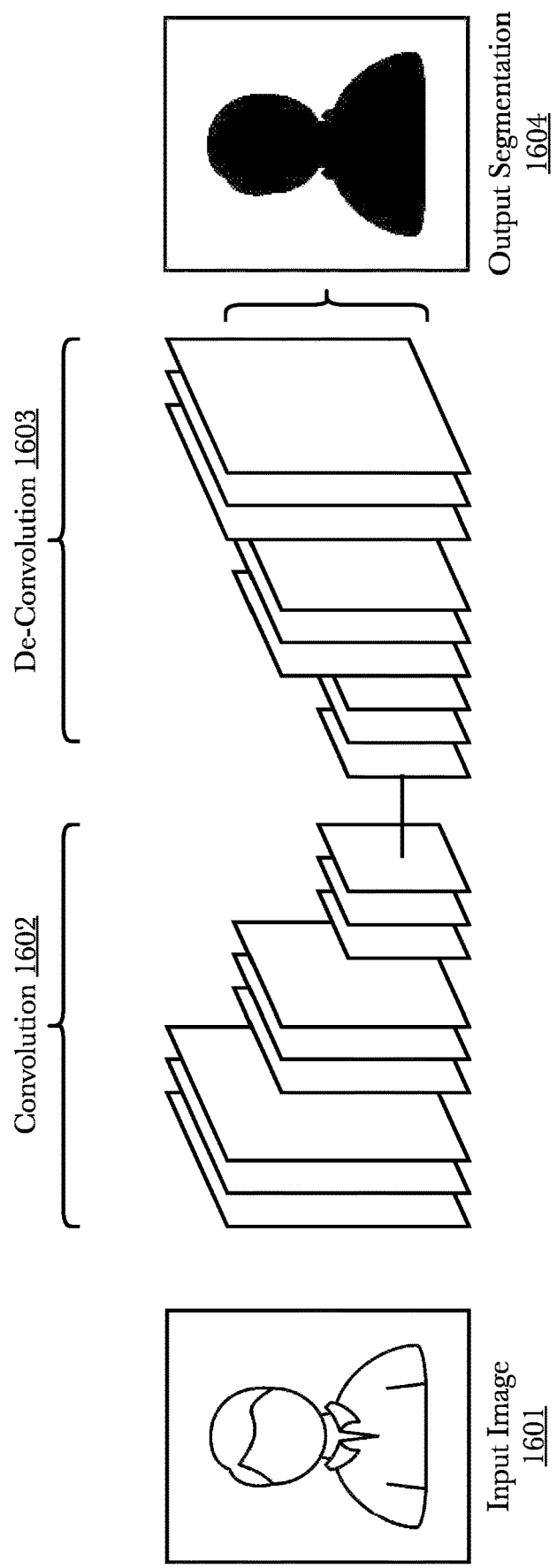
FIG. 16 (PRIOR ART) is a diagram describing the use of a convolutional neural network (CNN) to identify objects in an image by segmenting the objects from the background of the image.

FIG. 16 (PRIOR ART) is a diagram describing the use of a convolutional neural network (CNN) to identify objects in an image by segmenting the objects from the background of the image. Artificial neural networks are computing systems that mimic the function of the biological neural networks that constitute human and animal brains. Artificial neural networks comprise a series of "nodes" which loosely model the neurons in the brain. Each node can pass on a signal to other nodes. The output of each node is some non-linear function of the sum of its inputs, and the probability of a signal being passed to another node depends on the weight assigned to the "edge" between the nodes, which is the connection between the nodes. An artificial neural network finds the correct mathematical relationship between an input and an output by calculating a probability of obtaining the output from the input at each "layer" of mathematical calculations.

Convolutional neural networks are a type of artificial neural network commonly used to analyze imagery that use a mathematical operation called convolution (also called a dot product or cross-correlation) instead of general matrix multiplication as in other types of artificial neural networks. Convolutional neural networks are fully connected, meaning that each node in one layer is connected to every node in the next layer. Each layer of the CNN convolves the input from the previous layer. Each convolutional node processes data only for its receptive field, which is typically a small sub-area of the image (e.g., a 5×5 square of pixels). There may be pooling layers in a CNN which reduce the dimensionality of the data by combining the outputs of node clusters in one layer into a single node in the next layer. Each node in a CNN computes an output value by applying a specific function to the input values coming from the receptive field in the previous layer. The function that is applied to the input values is determined by a vector of weights and a bias. The CNN "learns" by making iterative adjustments to these biases and weights.

In this application of CNNs, an input image 1601 is processed through a CNN in which there are two stages, a convolution stage 1602 and a de-convolution stage 1603, ultimately resulting in an output image 1604 in which objects in the image are segmented (i.e., identified as separate from) the background of the image. In the convolution stage 1602, the image is processed through multiple convolution layers to extract features from the image, and then through a pooling layer to reduce the dimensionality of the data (i.e., aggregation of pixels) for the next round of convolutions. After several rounds of convolution and pooling, the features have been extracted and the data have been reduced to a manageable size. The data are then passed to the de-convolution stage 1603, in which a prediction is made as to whether each pixel or group of pixels represents an object and passed through several layers of de-convolution before a new prediction is made at a larger level of de-aggregation of the pixels. This process repeats until an output image 1604 is obtained of a similar size as the input image 1601, wherein each pixel of the output image 1604 is labeled with an indication as to whether it represents an object or background.

Figure 17:
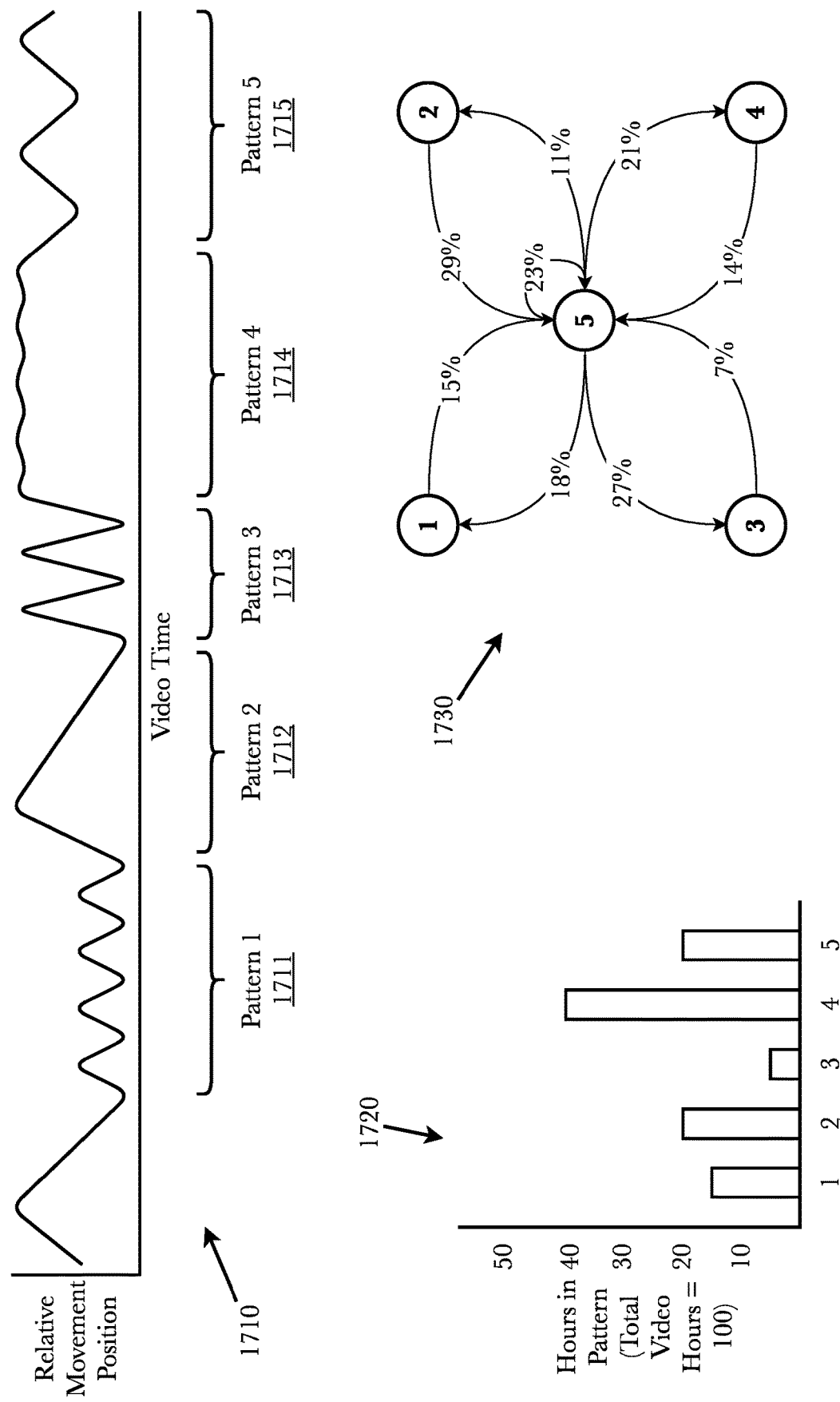
FIG. 17 is a diagram showing exemplary video annotation data collection and processing to develop models of sexual activity sequences.

FIG. 17 is a diagram showing exemplary video annotation data collection and processing to develop models of sexual activity sequences. In a first step, annotation data from videos depicting sexual activity is gathered. The diagram at 1710 shows an exemplary graph created from annotation data from a single video depicting sexual activity. The graph of the annotation data shows the relative position of an object in a single video over time (i.e., movement of the object over time in that video). A number of patterns of movement 1711-1715 can be seen in the graph. When used in conjunction with a single video, the annotation data can be converted directly into device control data for a sexual stimulation device, and the device can be used in synchronization with the video just from the annotation data for that video. However, if models of sexual activity are to be created for use with the sexual stimulation device (e.g., to mimic "typical" sexual activities but without reference to a particular video), additional processing is required to develop models from the annotated data.

To process annotation data to develop models, patterns of movement will ideally be extracted from a larger number of videos. When a machine learning algorithm is fed the annotation data from many such videos, these patterns can be identified across the various videos, and the frequency of these patterns across all videos can be extracted, as shown in the bar chart at 1720. In this bar chart 1720, one hundred total hours of video time was processed through the machine learning algorithm, and the number of hours each pattern of movement 1711-1715 was displayed is shown. For example, Pattern 4 was displayed in a total of 40 hours out of the 100 total hours of video. Machine learning algorithms suitable for this identification of patterns across videos are clustering-type algorithms such as K-means clustering (also known as Lloyd's algorithm), in which movement patterns in the annotation data are clustered into groups containing similar movement patterns. From the clusters, certain types of movement patterns can be identified. For example, in the case of a video depicting fellatio, clusters of movement will show shallow motions around the tip of the penis (e.g., Pattern 4 1714), deep motions around the base of the penis (e.g., Pattern 1), movements along the full length of the penis (e.g., Pattern 3), etc. Such clusters may be visually mapped in 2D or 3D to confirm the consistency and accuracy of the clustering.

Finally, other types of machine learning algorithms may be employed to create models of sexual activity shown in the processed annotation data. In one method, reinforcement learning may be employed to identify the frequency counts of certain patterns of movement, create "states" representing these patterns, and probabilities of transferring from any given state to any other state. An example of such a state diagram is shown at 1730, wherein each state represents one of the patterns of movement 1711-1715, and the lines and percentages indicate the probability of transitioning to a different state. In the diagram at 1730, Pattern 5 1715 is shown as the current state, and probabilities of all possible transitions to and from the current state are shown. In practice, this state diagram 1730 would be expanded to include the probabilities to and from each state to every other state, but this diagram is simplified to show only transitions to and from the current state. From these state transition probabilities, sequences of movement patterns 1711-1715 may be constructed representing models of the "typical" activities shown in the video. If annotation data are processed for selected types of videos (e.g., videos containing certain types of sexual activity, certain actors or actresses, or videos from a certain film studio or director, etc.), the models will be representative of that selected type of video. Alternatively, a wide variety of deep learning algorithms may be used for this process including, but not limited to, dense neural networks, convolutional neural networks, generative adversarial networks, and recurrent neural networks. Each of these types of machine learning algorithms may be employed to identify sequences of the patterns of movement identified in the clustering at the previous stage.

Figure 18:
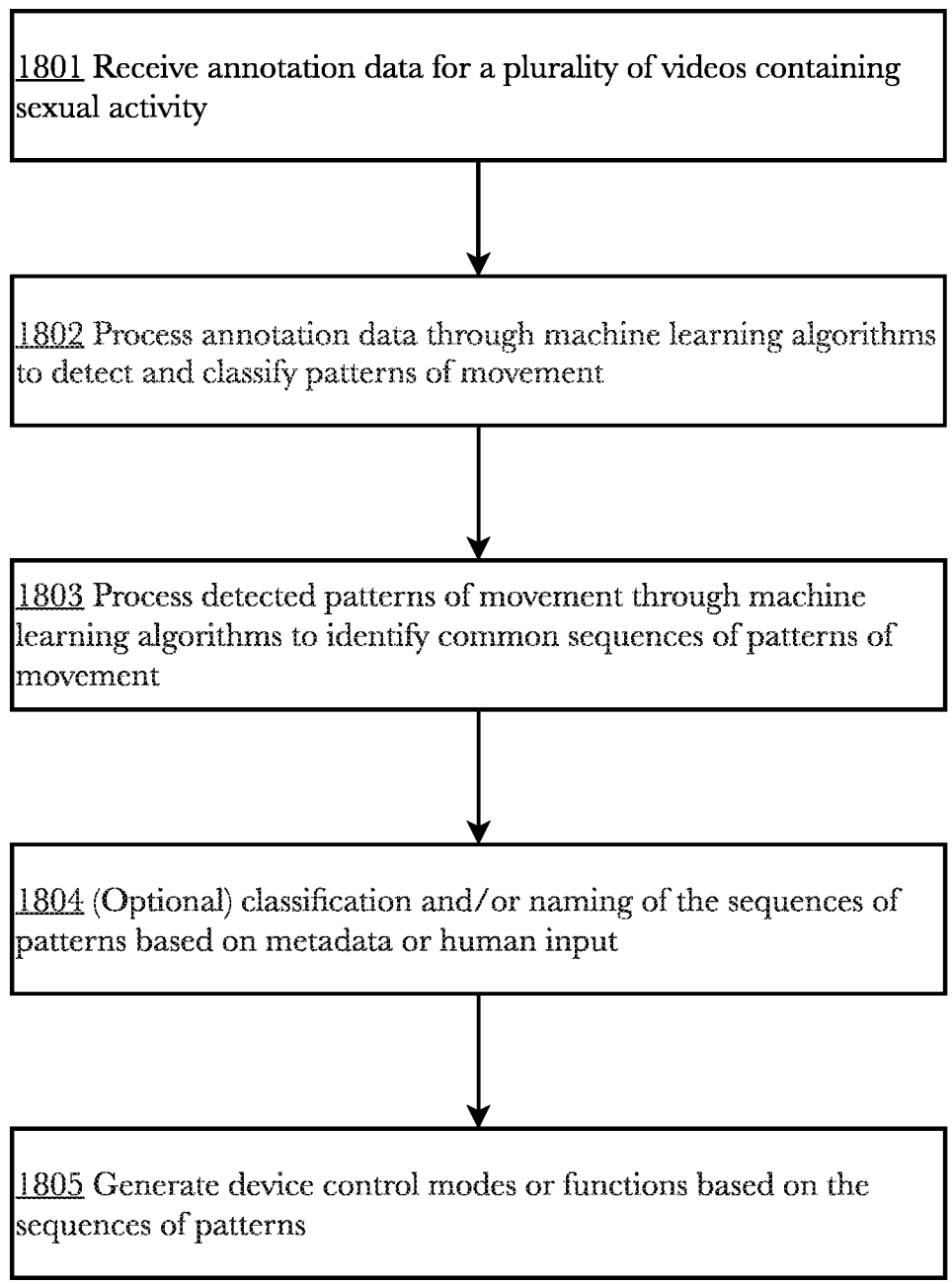
FIG. 18 is a flow diagram showing a method for an exemplary synchronized video control system for sexual stimulation devices.

FIG. 18 is a flow diagram showing a method for developing models of sexual activity sequences from selected videos. In a first step, annotation data are received for a plurality of videos of a particular type (e.g., videos containing certain types of sexual activity, certain actors or actresses, or videos from a certain film studio or director, etc.) 1801. Next, the annotation data are processed machine learning algorithms to detect and classify patterns of movement 1802. Then, the detected patterns of movement are further processed through machine learning algorithms to identify sequences of patterns of movement that are common for that selected type of video 1803, which are then turned into models representative of the types of sexual activity depicted. Optionally, the patterns and sequences of movement may be classified based on metadata associated with the video or based on human input 1804. For example, a particular sequence may be classified as a typical representation of fellatio by a particular adult film star from a certain decade. Lastly, after the models are created, device control modes or functions based on the models may be created 1805 and stored for later use or programmed into the sexual stimulation device.

Figure 20:
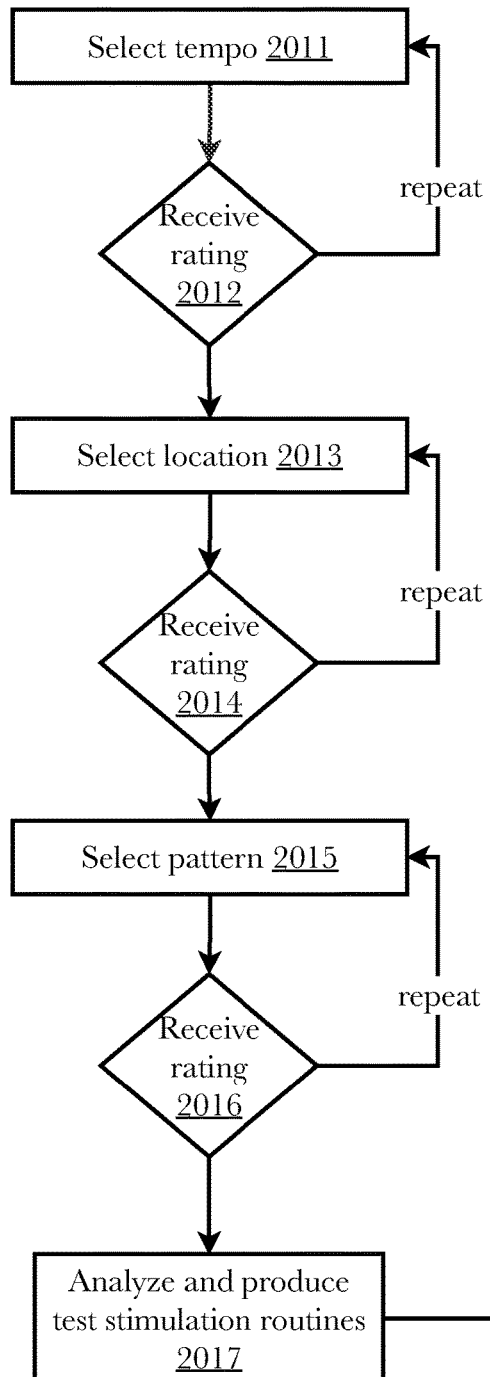
FIG. 20 is an exemplary algorithm for an automated set-up wizard for a system for automated control of sexual stimulation devices.
Figure 20:
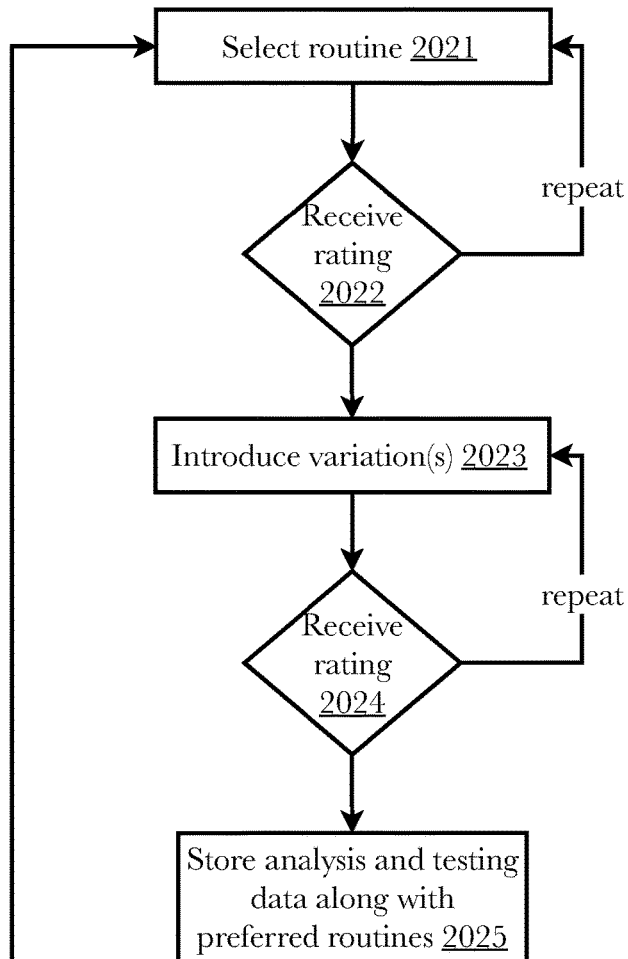

FIG. 20 is an exemplary algorithm for an automated set-up wizard for a system for automated control of sexual stimulation devices. The set-up wizard application 1922 builds an initial personalized stimulation profile from a series of ratings by the user of test stimulations. Completion of the set-up wizard application 1922 process accelerates customization of a stimulation profile for the user by providing a base set of ratings of various aspects of stimulation which can then be processed through the trained machine learning algorithm 1912 to automatically control the stimulation device 1930. After completion of the set-up wizard application 1922, stimulation profiles for the user may continue to evolve from new user-specific data as described above.

In this embodiment, the set-up wizard application 1922 process has two stages, an analysis stage and a testing stage. At the analysis stage 2010 stimulation selections are made from a set of pre-programmed aspects such as tempo, location, and pattern, and the user's ratings for each selection are used by the machine learning algorithm 1912 to generate a stimulation routine comprising one or more tempos, locations, and patterns of stimulation. At the testing stage 2020, stimulation is performed using the generated stimulation routine, and the generated stimulation routine is refined through ratings by the user and, optionally, introduction of variations deemed likely to improve those ratings. Optionally, the generated stimulation routine may be displayed on a user interface such as that shown in FIG. 21, and additional refinements may be made by manual adjustments to the routine by the user using the user interface.

In this exemplary process, the process begins at the analysis stage 2010 with the system's selection of one or more tempos of stimulation 2011 from a set of pre-programmed (or randomly chosen) and user ratings 2012 for each selected tempo. On each attempt, the tempo is changed, and a new rating is obtained. For example, if the system selects a slow tempo, and the user gives it a low rating, the system may select a faster tempo for the next selection and rating. Once a tempo, or range of tempos, is established, the system goes through the same process for location 2013 and user ratings associated with location 2014 using that tempo, and again with patterns of stimulation 2015 and user ratings 2016 based around the established tempo and established location. For a device capable of producing linear stroking motions, the patterns of stimulation may include, but are not limited to, variations in the established tempo, variations in the established location, stopping or starting of stimulation at various timings, and stimulation outside of the established tempo and established location for a period of time before returning to them. The user's ratings of the tempo, location, and patterns of stimulation are processed through the machine learning algorithm 1912 to generate one or more test stimulation routines 2017 for testing. At the testing stage 2020, a routine is selected 2021 from the one or more test stimulation routines 2017 and rated by the user 2022. This process may be repeated for several test stimulation routines 2017. In some cases (for example when only a single test stimulation routine is generated or where the test routines are all rated poorly by the user), the system may introduce variations in one or more of the test routines 2023 in an attempt to increase the user's rating 2024 of that test routine. The variations come from any number of sources, including but not limited to, a list of known variations, variations generated by the machine learning algorithm 1912, and random variation. Once the testing stage 2020 is completed, one or more preferred stimulation routines are stored, along with the analysis and testing data for future use 2025.

Figure 21:
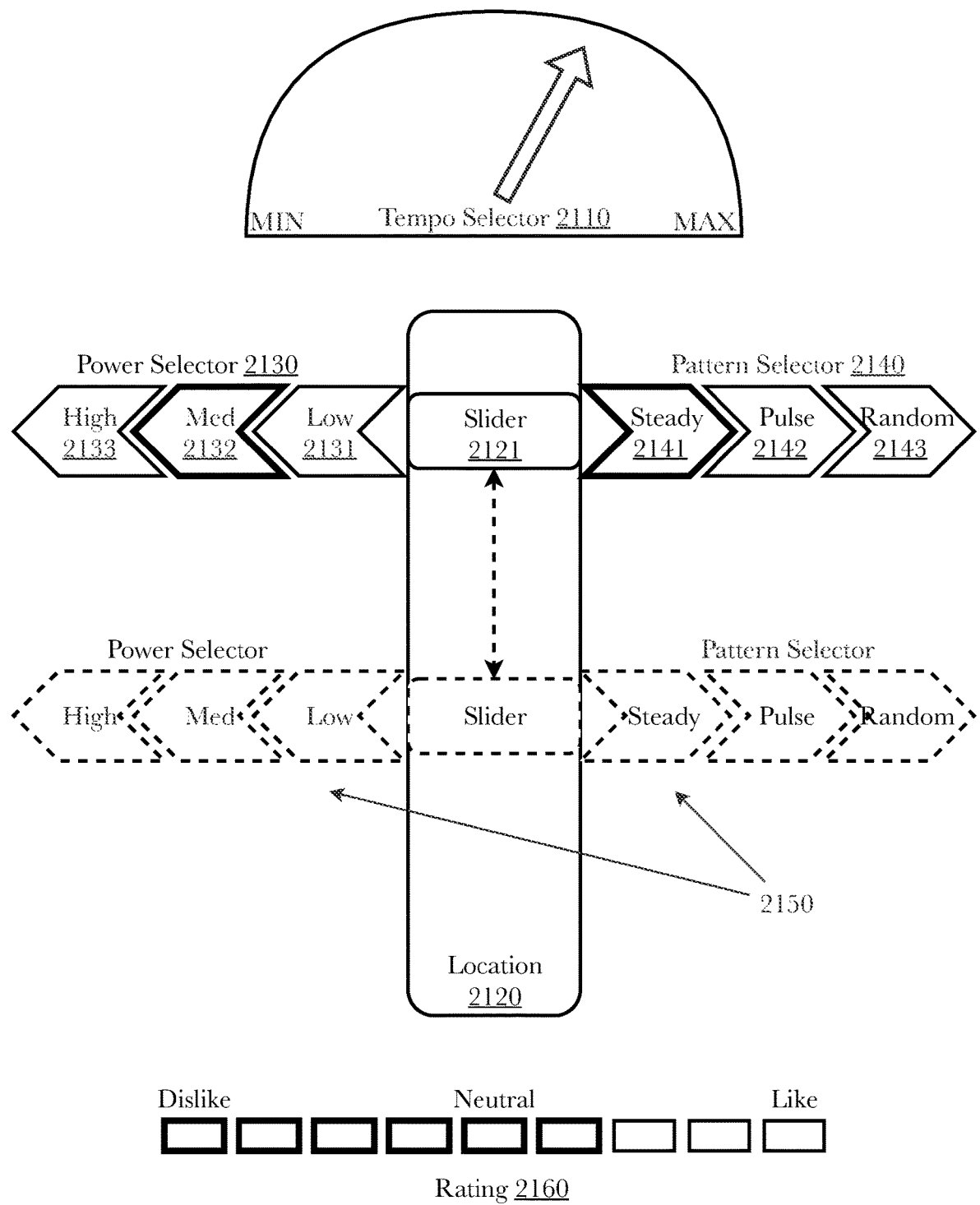
FIG. 21 is an exemplary screenshot of a user interface for viewing, adjustment, and rating of automated control settings for a sexual stimulation device.

FIG. 21 is an exemplary screenshot of a user interface for viewing, adjustment, and rating of automated control settings for a sexual stimulation device. During manual operation of the stimulation device 1930, various aspects of the current stimulation being provided by the stimulation device 1930 are displayed on an appropriate display or computing device, and the controls for each aspect may be adjusted by the user according to preference. During automated operation of the stimulation device 1930, various aspects of the operation of the stimulation device 1930 are displayed, reflecting the current stimulation routine. Each of the aspects displayed can be changed by the user to manually override the current settings, and the manually-overridden settings will be provided to the client application 1930 or server 1910 for adjustment of the current stimulation routine according (and for evolution of that user's preferred stimulation routines). During the set-up wizard application 1922 process, these displays and controls 2110-2160 may be used to adjust and rate the aspect of stimulation under test.

In this example, it is assumed that the current stimulation routine is being displayed on a mobile phone or tablet device with a touch screen, although the system is not so limited. In this screenshot, a tempo selector 2110 is shown with an arrow indicating the current tempo of stimulation on a range from minimum to maximum. The tempo arrow can be moved by the user to override the tempo setting of the current stimulation routine, and the override information will be forwarded to the client application or server 1910 for adjustment of the current stimulation routine and evolution of the user's stimulation preferences over time. A location selector 2120 is shown with an slider 2121 indicating the current location of stimulation (here on a device that provides stimulation using a reciprocal linear motion). The slider 2121 can be moved by the user to override the location setting of the current stimulation routine, and the override information will be forwarded to the client application or server 1910 for adjustment of the current stimulation routine and evolution of the user's stimulation preferences over time. At the location indicated by the slider 2121, a power selector 2130 displays the current power setting for that location and allows the user to adjust the power setting for that location, and a pattern selector 2140 displays the current pattern setting for that location and allows the user to adjust the pattern setting for that location. A different position of the slider is shown at 2150, along with the power selector 2130 and pattern selector 2140 for that different location. A rating bar 2160 is shown at the bottom of the screen, allowing the user to input a rating for the current stimulation.

Hardware Architecture

Generally, the techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of the aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of these machines may be described herein in order to illustrate one or more exemplary means by which a given unit of functionality may be implemented. According to specific aspects, at least some of the features or functionalities of the various aspects disclosed herein may be implemented on one or more general-purpose computers associated with one or more networks, such as for example an end-user computer system, a client computer, a network server or other server system, a mobile computing device (e.g., tablet computing device, mobile phone, smartphone, laptop, or other appropriate computing device), a consumer electronic device, a music player, or any other suitable electronic device, router, switch, or other suitable device, or any combination thereof. In at least some aspects, at least some of the features or functionalities of the various aspects disclosed herein may be implemented in one or more virtualized computing environments (e.g., network computing clouds, virtual machines hosted on one or more physical computing machines, or other appropriate virtual environments).

Figure 22:
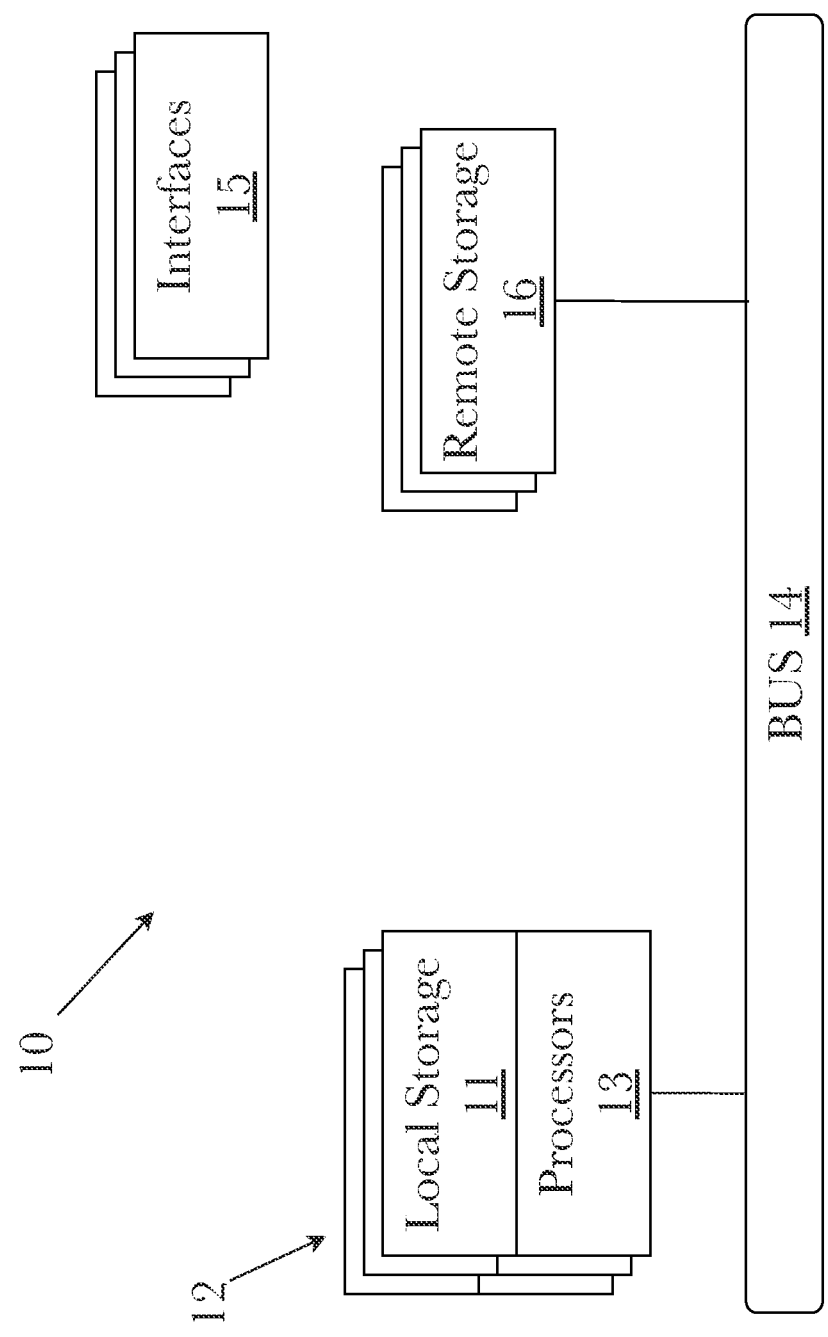
FIG. 22 is a block diagram illustrating an exemplary hardware architecture of a computing device.

Referring now to FIG. 22, there is shown a block diagram depicting an exemplary computing device 10 suitable for implementing at least a portion of the features or functionalities disclosed herein. Computing device 10 may be, for example, any one of the computing machines listed in the previous paragraph, or indeed any other electronic device capable of executing software- or hardware-based instructions according to one or more programs stored in memory. Computing device 10 may be configured to communicate with a plurality of other computing devices, such as clients or servers, over communications networks such as a wide area network a metropolitan area network, a local area network, a wireless network, the Internet, or any other network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under the control of appropriate software or firmware, CPU 12 may be responsible for implementing specific functions associated with the functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of the different types of functions and/or operations under the control of software modules or components, which for example, may include an operating system and any appropriate applications software, drivers, and the like.

CPU 12 may include one or more processors 13 such as, for example, a processor from one of the Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, there are many different ways in which memory may be coupled to system 10.

Memory 11 may be used for a variety of purposes such as, for example, caching and/or storing data, programming instructions, and the like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in the art, such as for use in mobile devices or integrated devices.

As used herein, the term "processor" is not limited merely to those integrated circuits referred to in the art as a processor, a mobile processor, or a microprocessor, but broadly refers to a microcontroller, a microcomputer, a programmable logic controller, an application-specific integrated circuit, and any other programmable circuit.

In one aspect, interfaces 15 are provided as network interface cards (NICs). Generally, NICs control the sending and receiving of data packets over a computer network; other types of interfaces 15 may for example support other peripherals used with computing device 10. Among the interfaces that may be provided are Ethernet interfaces, frame relay interfaces, cable interfaces, DSL interfaces, token ring interfaces, graphics interfaces, and the like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and the like. Generally, such interfaces 15 may include physical ports appropriate for communication with appropriate media. In some cases, they may also include an independent processor (such as a dedicated audio or video processor, as is common in the art for high-fidelity A/V hardware interfaces) and, in some instances, volatile and/or non-volatile memory (e.g., RAM).

Although the system shown in FIG. 22 illustrates one specific architecture for a computing device 10 for implementing one or more of the aspects described herein, it is by no means the only device architecture on which at least a portion of the features and techniques described herein may be implemented. For example, architectures having one or any number of processors 13 may be used, and such processors 13 may be present in a single device or distributed among any number of devices. In one aspect, a single processor 13 handles communications as well as routing computations, while in other aspects a separate dedicated communications processor may be provided. In various aspects, different types of features or functionalities may be implemented in a system according to the aspect that includes a client device (such as a tablet device or smartphone running client software) and server systems (such as a server system described in more detail below).

Regardless of network device configuration, the system of an aspect may employ one or more memories or memory modules (such as, for example, remote memory block 16 and local memory 11) configured to store data, program instructions for the general-purpose network operations, or other information relating to the functionality of the aspects described herein (or any combinations of the above). Program instructions may control execution of or comprise an operating system and/or one or more applications, for example. Memory 16 or memories 11, 16 may also be configured to store data structures, configuration data, encryption data, historical system operations information, or any other specific or generic non-program information described herein.

Because such information and program instructions may be employed to implement one or more systems or methods described herein, at least some network device aspects may include nontransitory machine-readable storage media, which, for example, may be configured or designed to store program instructions, state information, and the like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in the art with regard to personal computers), memristor memory, random access memory (RAM), and the like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or other removable media designed for rapidly exchanging physical storage devices), "hot-swappable" hard disk drives or solid state drives, removable optical storage discs, or other such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by the computer using an interpreter (for example, scripts written in Python, Perl, Ruby, Groovy, or any other scripting language).

Figure 23:
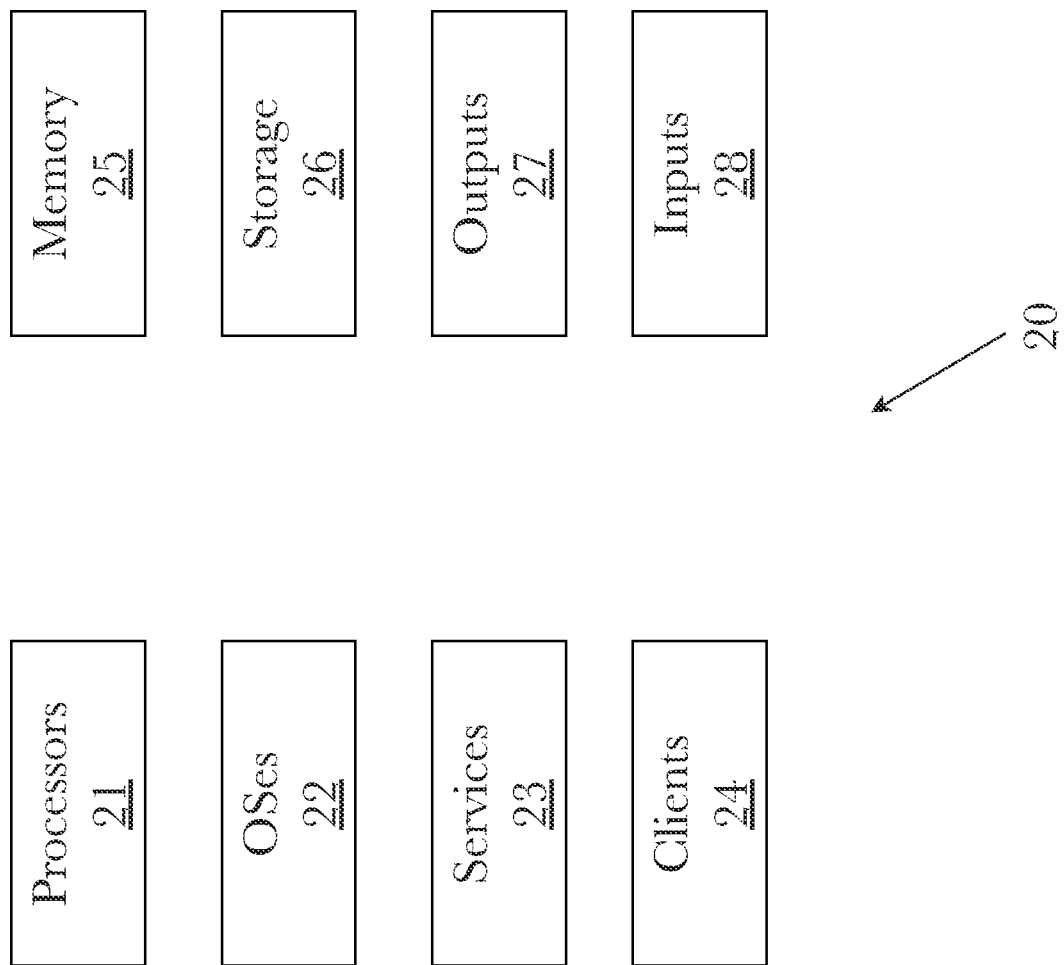
FIG. 23 is a block diagram illustrating an exemplary logical architecture for a client device.

In some aspects, systems may be implemented on a standalone computing system. Referring now to FIG. 23, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of the Linux operating system, ANDROID™ operating system, or the like. In many cases, one or more shared services 23 may be operable in system 20, and may be useful for providing common services to client applications 24. Services 23 may for example be WINDOWS™ services, user-space common services in a Linux environment, or any other type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, whether remote or local to system 20, and may include for example one or more screens for visual output, speakers, printers, or any combination thereof. Memory 25 may be random-access memory having any structure and architecture known in the art, for use by processors 21, for example to run software. Storage devices 26 may be any magnetic, optical, mechanical, memristor, or electrical storage device for storage of data in digital form (such as those described above, referring to FIG. 22). Examples of storage devices 26 include flash memory, magnetic hard drive, CD-ROM, and/or the like.

Figure 24:
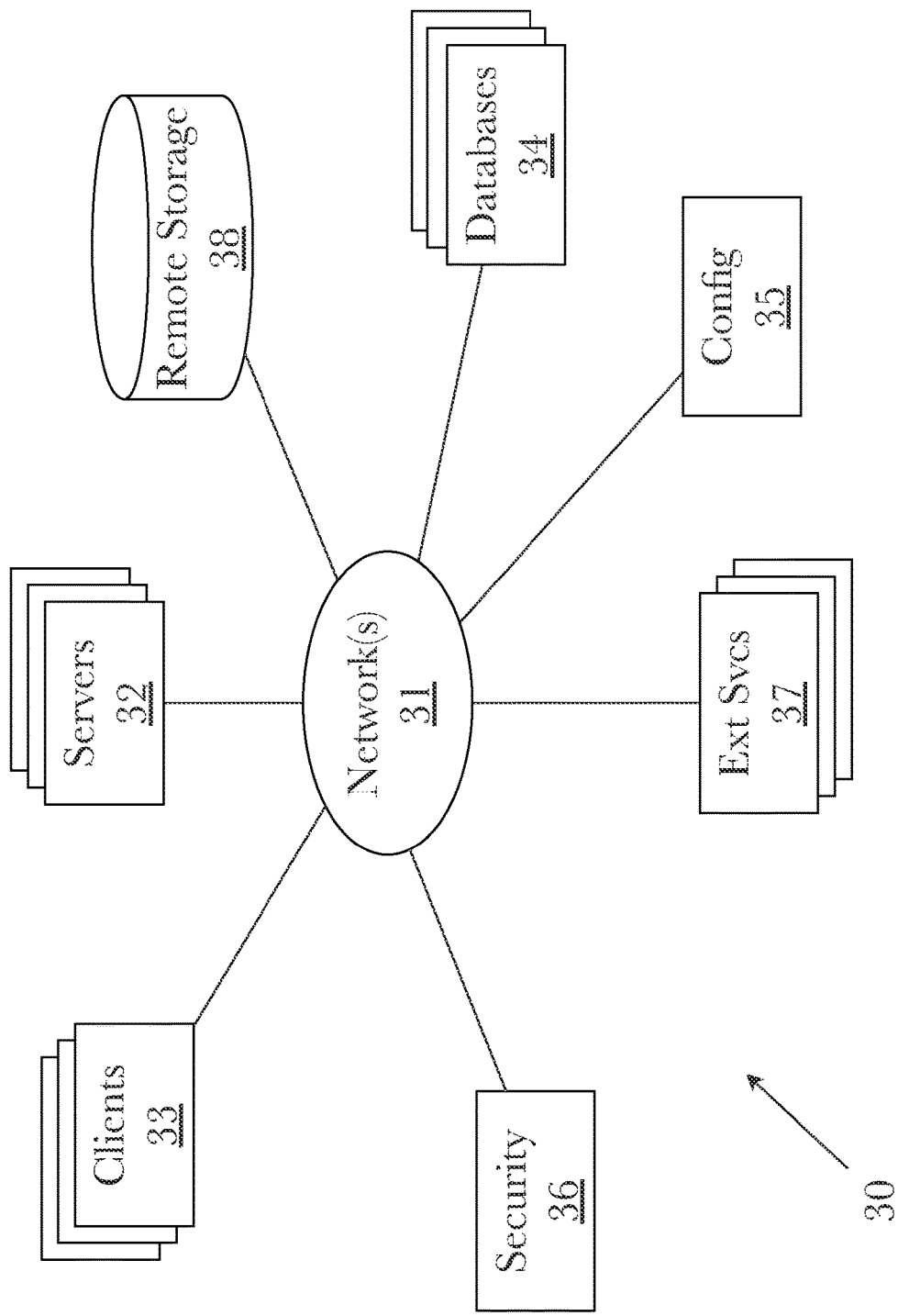
FIG. 24 is a block diagram showing an exemplary architectural arrangement of clients, servers, and external services.

In some aspects, systems may be implemented on a distributed computing network, such as one having any number of clients and/or servers. Referring now to FIG. 24, there is shown a block diagram depicting an exemplary architecture 30 for implementing at least a portion of a system according to one aspect on a distributed computing network. According to the aspect, any number of clients 33 may be provided. Each client 33 may run software for implementing client-side portions of a system; clients may comprise a system 20 such as that illustrated in FIG. 23. In addition, any number of servers 32 may be provided for handling requests received from one or more clients 33. Clients 33 and servers 32 may communicate with one another via one or more electronic networks 31, which may be in various aspects any of the Internet, a wide area network, a mobile telephony network (such as CDMA or GSM cellular networks), a wireless network (such as WiFi, WiMAX, LTE, and so forth), or a local area network (or indeed any network topology known in the art; the aspect does not prefer any one network topology over any other). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on the hardware device itself. For example, in one aspect where client applications 24 are implemented on a smartphone or other electronic device, client applications 24 may obtain information stored in a server system 32 in the cloud or on an external service 37 deployed on one or more of a particular enterprise's or user's premises. In addition to local storage on servers 32, remote storage 38 may be accessible through the network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in the art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in the art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to the aspect. It will be appreciated by one having ordinary skill in the art that any combination of known or future database technologies may be used as appropriate, unless a specific database technology or a specific arrangement of components is specified for a particular aspect described herein. Moreover, it should be appreciated that the term "database" as used herein may refer to a physical database machine, a cluster of machines acting as a single database system, or a logical database within an overall database management system. Unless a specific meaning is specified for a given use of the term "database", it should be construed to mean any of these senses of the word, all of which are understood as a plain meaning of the term "database" by those having ordinary skill in the art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in the art that any configuration or security subsystems known in the art now or in the future may be used in conjunction with aspects without limitation, unless a specific security 36 or configuration system 35 or approach is specifically required by the description of any specific aspect.

Figure 25:
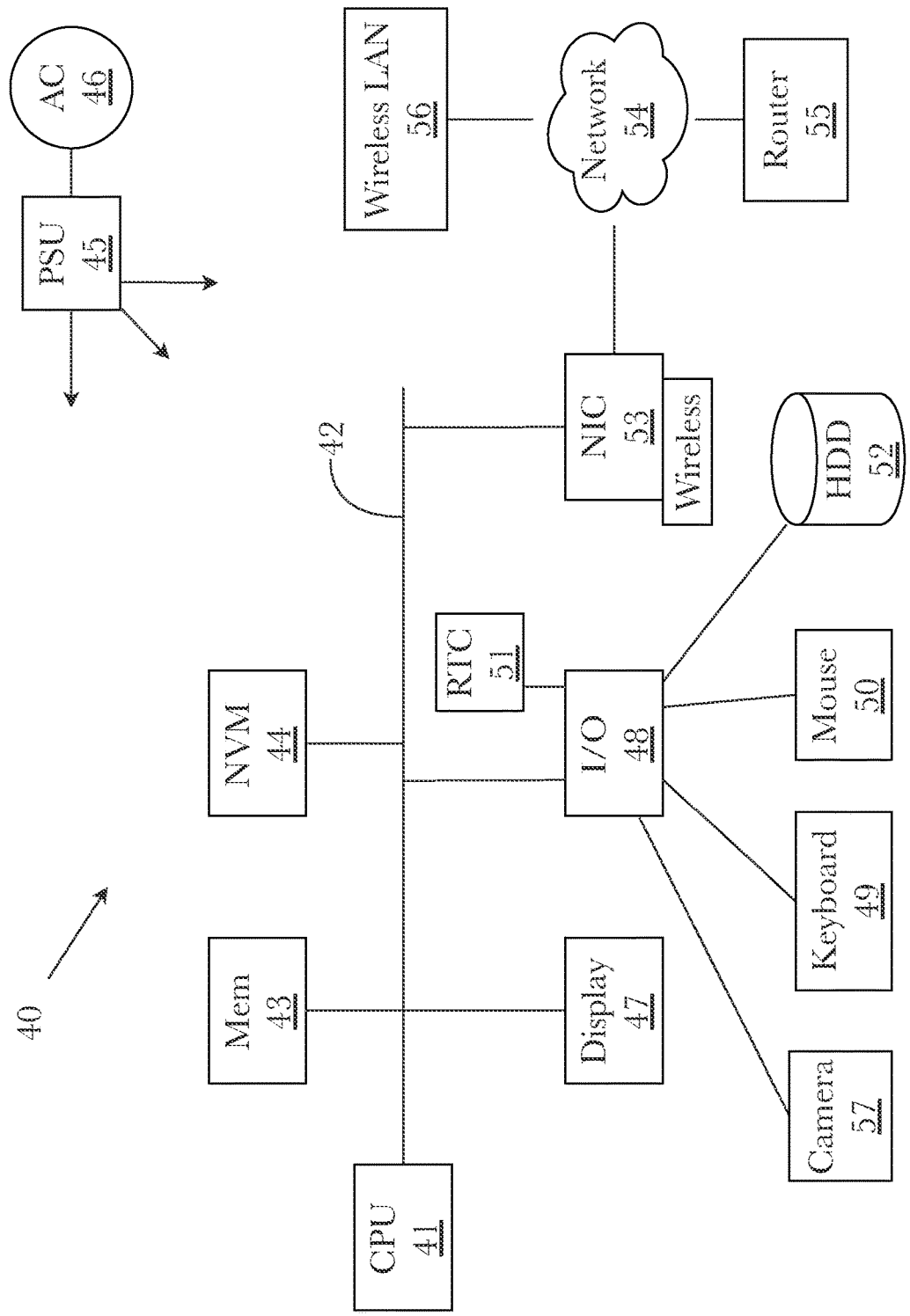
FIG. 25 is another block diagram illustrating an exemplary hardware architecture of a computing device.

FIG. 25 shows an exemplary overview of a computer system 40 as may be used in any of the various locations throughout the system. It is exemplary of any computer that may execute code to process data. Various modifications and changes may be made to computer system 40 without departing from the broader scope of the system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and other peripheral devices. NIC 53 connects to network 54, which may be the Internet or a local network, which local network may or may not have connections to the Internet. The system may be connected to other computing devices through the network via a router 55, wireless local area network 56, or any other network connection. Also shown as part of system 40 is power supply unit 45 connected, in this example, to a main alternating current (AC) supply 46. Not shown are batteries that could be present, and many other devices and modifications that are well known but are not applicable to the specific novel functions of the current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or other integrated hardware devices).

In various aspects, functionality for implementing systems or methods of various aspects may be distributed among any number of client and/or server components. For example, various software modules may be implemented for performing various functions in connection with the system of any particular aspect, and such modules may be variously implemented to run on server and/or client components.

The skilled person will be aware of a range of possible modifications of the various aspects described above. Accordingly, the present invention is defined by the claims and their equivalents.

What is claimed is:

1. A system for automated generation of initial stimulation profiles for sexual stimulation devices from testing and user feedback, comprising:
   a computing device comprising a memory, a processor, and a non-volatile data storage device;
   a machine learning algorithm operating on the computing device, wherein the machine learning algorithm is trained to identify patterns among user feedback for a given type of stimulation device and further configured to output learned stimulation profiles based on learned patterns; and
   a setup wizard application comprising a first plurality of programming instructions stored in the memory which, when operating on the processor, causes the computing device to:
   connect to a device controller for a stimulation device of the given type of stimulation device;
   operate the stimulation device according to one or more learned stimulation profiles for the given type of stimulation device, and receive feedback from a user of the stimulation device for each of the one or more learned stimulation profiles;
   process the one or more learned stimulation profiles and the feedback for each of the one or more learned stimulation profiles through the machine learning algorithm to obtain an initial stimulation profile for the user;
   operate the stimulation device according to the initial stimulation profile;
   receive feedback for the initial stimulation profile; and
   if the feedback for the initial stimulation profile reaches a threshold level of satisfaction, store the initial stimulation profile in a user profile created for the user;
   otherwise, adjust the initial stimulation profile and operate the stimulation device according to the adjusted initial stimulation profile until the feedback for the initial stimulation profile reaches the threshold level of satisfaction, and store the adjusted initial stimulation profile in the user profile created for the user.

2. The system of claim 1, wherein the feedback for the initial stimulation profile comprises sensor data from a sensor on the stimulation device, wherein the sensor data is received from the controller via a wireless networking device.

3. The system of claim 1, wherein the setup wizard application is configured to connect to an external device other than the stimulation device, and the feedback for the initial stimulation profile comprises data from a sensor on the external device.

4. The system of claim 1, further comprising a user interface operating on the computing device, the user interface comprising operational controls for the stimulation device or rating controls for the initial stimulation profile, and wherein the feedback for the initial stimulation profile is received from the user via the user interface.

5. The system of claim 1, further comprising an auto-pilot application comprising a second plurality of programming instructions stored in the memory which, when operating on the processor, causes the computing device to:
   (a) receive a first user profile for a user of a stimulation device of the given type of stimulation device from a user profile database;
   (b) process the first user profile through the machine learning algorithm to obtain a stimulation profile for the user associated with the first user profile;
   (c) generate control signals for the stimulation device based on the stimulation profile;
   (d) connect to the device controller for the stimulation device using the wireless networking device and output the control signals to the device controller using the wireless networking device;
   (e) receive feedback associated with the stimulation profile;
   (f) update the first user profile with the feedback received in step (e); and
   (g) repeat steps (a) through (f) for the updated user profile.

6. A system for automated generation of initial stimulation profiles for sexual stimulation devices from testing and user feedback, comprising:
   a distributed computing network comprising a plurality of networked computers, each computer comprising a memory, a processor, a non-volatile data storage device, and a wireless networking device;
   a machine learning algorithm operating on one of the plurality of networked computers, wherein the machine learning algorithm is trained to identify patterns among user feedback for a given type of stimulation device and further configured to output learned stimulation profiles based on learned patterns; and
   a setup wizard application operating on a first computer of the plurality of networked computers, the setup wizard application comprising a first plurality of programming instructions stored in the memory of the first computer which, when operating on the processor of the first computer, causes the first computer to:
   connect to a device controller for a stimulation device of the given type of stimulation device;
   operate the stimulation device according to one or more learned stimulation profiles for the given type of stimulation device, and receive feedback from a user of the stimulation device for each of the one or more learned stimulation profiles;
   process the one or more learned stimulation profiles and the feedback for each of the one or more learned stimulation profiles through the machine learning algorithm to obtain an initial stimulation profile for the user;
   operate the stimulation device according to the initial stimulation profile;
   receive feedback for the initial stimulation profile; and
   if the feedback for the initial stimulation profile reaches a threshold level of satisfaction, store the initial stimulation profile in a user profile created for the user;
   otherwise, adjust the initial stimulation profile and operate the stimulation device according to the adjusted initial stimulation profile until the feedback for the initial stimulation profile reaches the threshold level of satisfaction, and store the adjusted initial stimulation profile in the user profile created for the user.

7. The system of claim 6, wherein the feedback for the initial stimulation profile comprises sensor data from a sensor on the stimulation device, wherein the sensor data is received from the controller via the wireless networking device.

8. The system of claim 6, wherein the setup wizard application is configured to connect to an external device other than the stimulation device, and the feedback for the initial stimulation profile comprises data from a sensor on the external device.

9. The system of claim 6, further comprising a user interface operating one of the plurality of networked computers, the user interface comprising operational controls for the stimulation device or rating controls for the initial stimulation profile, and wherein the feedback for the initial stimulation profile is received from the user via the user interface.

10. The system of claim 6, further comprising an auto-pilot application comprising a second plurality of programming instructions stored in at least one of the memories which, when operating on at least one of the processors, causes one of the plurality of networked computers to:
  (a) receive a first user profile for a user of a stimulation device of the given type of stimulation device from a user profile database;
  (b) process the first user profile through the machine learning algorithm to obtain a stimulation profile for the user associated with the first user profile;
  (c) generate control signals for the stimulation device based on the stimulation profile;
  (d) connect to the device controller for the stimulation device using the wireless networking device and output the control signals to the device controller using the wireless networking device;
  (e) receive feedback associated with the stimulation profile;
  (f) update the first user profile with the feedback received in step (e); and
  (g) repeat steps (a) through (f) for the updated user profile.

11. A method for automated generation of initial stimulation profiles for sexual stimulation devices from testing and user feedback, comprising the steps of:
  training a machine learning algorithm, operating on a computing device, to identify patterns among user feedback for a given type of stimulation device, wherein the machine learning algorithm is further configured to output learned stimulation profiles based on learned patterns; and
  using a setup wizard application operating on the computing device to:
    connect to a device controller for a stimulation device of the given type of stimulation device;
    operate the stimulation device according to one or more learned stimulation profiles for the given type of stimulation device, and receive feedback from a user of the stimulation device for each of the one or more learned stimulation profiles;
    process the one or more learned stimulation profiles and the feedback for each of the one or more learned stimulation profiles through the machine learning algorithm to obtain an initial stimulation profile for the user;
    operate the stimulation device according to the initial stimulation profile;
    receive feedback for the initial stimulation profile; and
    if the feedback for the initial stimulation profile reaches a threshold level of satisfaction, store the initial stimulation profile in a user profile created for the user;
    otherwise, adjust the initial stimulation profile and operate the stimulation device according to the adjusted initial stimulation profile until the feedback for the initial stimulation profile reaches the threshold level of satisfaction, and store the adjusted initial stimulation profile in the user profile created for the user.

12. The method of claim 11, wherein the feedback for the initial stimulation profile comprises sensor data from a sensor on the stimulation device, wherein the sensor data is received from the controller via a wireless networking device.

13. The method of claim 11, wherein the setup wizard application is configured to connect to an external device other than the stimulation device, and the feedback for the initial stimulation profile comprises data from a sensor on the external device.

14. The method of claim 11, further comprising a user interface operating on the computing device, the user interface comprising operational controls for the stimulation device or rating controls for the initial stimulation profile, and wherein the feedback for the initial stimulation profile is received from the user via the user interface.

15. The method of claim 11, further comprising the steps of using an auto-pilot application operating on the computing device to:
  (a) receive a first user profile for a user of a stimulation device of the given type of stimulation device from a user profile database;
  (b) process the first user profile through the machine learning algorithm to obtain a stimulation profile for the user associated with the first user profile;
  (c) generate control signals for the stimulation device based on the stimulation profile;
  (d) connect to the device controller for the stimulation device using a wireless networking device and output the control signals to the device controller using the wireless networking device;
  (e) receive feedback associated with the stimulation profile;
  (f) update the first user profile with the feedback received in step (e); and
  (g) repeat steps (a) through (f) for the updated user profile.

\* \* \* \* \*

UNITED STATES PATENT AND TRADEMARK OFFICE
CERTIFICATE OF CORRECTION

| | |
|---|---|
| PATENT NO. | : 11,766,380 B2 |
| APPLICATION NO. | : 18/183948 |
| DATED | : September 26, 2023 |
| INVENTOR(S) | : Brian Sloan |

It is certified that error appears in the above-identified patent and that said Letters Patent is hereby corrected as shown below:

On the Title Page

Item (73) "Assignee: BOON INTELLECTUAL PROPERTY LAW, PLLC" is hereby deleted.

Signed and Sealed this
Sixteenth Day of April, 2024

Katherine Kelly Vidal
*Director of the United States Patent and Trademark Office*